United States Patent
Amamiya et al.

(10) Patent No.: US 11,099,127 B2
(45) Date of Patent: Aug. 24, 2021

(54) NONDESTRUCTIVE MEASUREMENT APPARATUS

(71) Applicant: ATAGO CO., LTD., Tokyo (JP)

(72) Inventors: Hideyuki Amamiya, Tokyo (JP); Masanosuke Tanaka, Tokyo (JP); Tomohiro Kiire, Tokyo (JP); Junji Higuchi, Saitama (JP)

(73) Assignee: ATAGO CO., LTD., Tokyo (JP)

(*) Notice: Subject to any disclaimer, the term of this patent is extended or adjusted under 35 U.S.C. 154(b) by 0 days.

(21) Appl. No.: 15/775,503

(22) PCT Filed: Jan. 20, 2017

(86) PCT No.: PCT/JP2017/001848
§ 371 (c)(1),
(2) Date: May 11, 2018

(87) PCT Pub. No.: WO2018/047366
PCT Pub. Date: Mar. 15, 2018

(65) Prior Publication Data
US 2019/0003963 A1    Jan. 3, 2019

(30) Foreign Application Priority Data

Sep. 6, 2016  (JP) .............................. JP2016-173529

(51) Int. Cl.
*G01N 21/359* (2014.01)
*G01N 21/3563* (2014.01)
(Continued)

(52) U.S. Cl.
CPC ....... *G01N 21/359* (2013.01); *G01N 21/3563* (2013.01); *G01N 21/59* (2013.01);
(Continued)

(58) Field of Classification Search
CPC .. G01N 21/359; G01N 21/3563; G01N 21/59; G01N 33/025; G01N 2201/0221; G01N 2021/8466
See application file for complete search history.

(56) References Cited

U.S. PATENT DOCUMENTS 6,504,154 B2   1/2003   Iida et al.
7,982,189 B2   7/2011   Fournel et al.
(Continued)

FOREIGN PATENT DOCUMENTS

AU        2123901 A1     10/2001
CN     101821611 A       9/2010
(Continued)

OTHER PUBLICATIONS

Yoneda—JP 2882824 B2—Google Patents English Translation obtained Dec. 5, 2019, pp. 1-4 (Year: 2019).*
(Continued)

*Primary Examiner* — David P Porta
*Assistant Examiner* — Jeremy S Valentiner
(74) *Attorney, Agent, or Firm* — Greenblum & Bernstein, P.L.C.

(57) ABSTRACT

A nondestructive measurement apparatus includes a casing including a grip portion capable of being held in hand and a measurement portion having a ring shaped abutting portion to be abutted to a measurement target such as fruit or vegetable; a light source group including a plurality of light sources arranged to be separated in a circumferential direction in an interior thereof; a ring lens arranged in a ring shape smaller than the abutting portion at an inner portion of the abutting portion, for emitting lights from the light source group to an external of the casing in a ring shape; and a light guide member having one end surface exposed to an inner side of the ring lens and another end surface positioned in (Continued)

the interior of the casing, for emitting lights incident from the one end surface to the external from the another end surface.

5 Claims, 17 Drawing Sheets

(51) Int. Cl.
*G01N 33/02* (2006.01)
*G01N 21/84* (2006.01)
*G01N 21/59* (2006.01)

(52) U.S. Cl.
CPC ... *G01N 33/025* (2013.01); *G01N 2021/8466* (2013.01); *G01N 2201/0221* (2013.01)

(56) References Cited

U.S. PATENT DOCUMENTS

| | | | |
|---|---|---|---|
| 8,964,180 B2 | 2/2015 | Pellenc et al. | |
| 2001/0045517 A1* | 11/2001 | Iida | G01N 33/025 250/339.06 |
| 2003/0147254 A1 | 8/2003 | Yoneda et al. | |
| 2003/0169421 A1 | 9/2003 | Ehbets | |
| 2004/0130720 A1 | 7/2004 | Maeda et al. | |
| 2004/0149916 A1 | 8/2004 | Benedetti et al. | |
| 2010/0252737 A1 | 10/2010 | Fournel et al. | |
| 2012/0050683 A1* | 3/2012 | Yates | H04N 5/2251 351/219 |
| 2012/0092619 A1* | 4/2012 | Rowe | A61B 3/0016 351/221 |
| 2012/0113209 A1* | 5/2012 | Ritchey | H04N 21/4305 348/14.02 |
| 2012/0140231 A1 | 6/2012 | Knox et al. | |
| 2012/0229809 A1* | 9/2012 | Pellenc | G01N 21/474 356/402 |
| 2014/0155757 A1 | 6/2014 | Yang et al. | |
| 2015/0021478 A1* | 1/2015 | Lee | G01N 33/025 250/338.4 |
| 2016/0313211 A1 | 10/2016 | Higuchi et al. | |

FOREIGN PATENT DOCUMENTS

| | | | | |
|---|---|---|---|---|
| CN | 102959382 A | | 3/2013 | |
| CN | 103687531 A | | 3/2014 | |
| CN | 105814423 | | 7/2016 | |
| EP | 1 635 374 | | 3/2006 | |
| IE | 20000608 | | 7/2001 | |
| IE | 20000608 A1 | * | 7/2001 | ............. G01N 21/88 |
| JP | 2882824 B2 | * | 4/1999 | ............. G01N 21/27 |
| JP | 2002-014042 | | 1/2002 | |
| JP | 2007-57296 | | 3/2007 | |
| JP | 2011-80959 | | 4/2011 | |
| JP | 2015-108508 | | 6/2015 | |
| TW | 201129795 | | 9/2011 | |
| TW | 201215873 | | 4/2012 | |
| WO | 02/088681 | | 11/2002 | |
| WO | 2011027052 A1 | | 3/2011 | |
| WO | 2012005350 | | 1/2012 | |
| WO | 2013/137145 A1 | | 9/2013 | |

OTHER PUBLICATIONS

Official Communication issued in Japan Patent Application No. PCT/JP2017/001848, dated Mar. 14, 2017.
European Search Report, European Patent Office, Application No. 17848313.7, dated Mar. 3, 2020 (in English).
Official Action in counterpart Taiwanese Patent Application No. 106102116, dated Dec. 5, 2019.
Taiwanese Office Action, Taiwanese Patent Office, in counterpart Taiwanese Patent Application No. 106102116, dated Mar. 16, 2021 (with machine English Translation).
European Office Action, European Patent Office, Application No. 17848313.7, dated Oct. 30, 2020.
Taiwanese Office Action, Taiwanese Patent Office, Application No. 106102116, dated Jul. 7, 2020.
Japanese Office Action, Japanese Patent Office, Application No. 2018-538004, dated Jul. 7, 2020.
Japanese Office Action, Japanese Patent Office, Application No. issued 2018-538004, dated Sep. 23, 2020.
Chinese Office Action, Chinese Patent Office, Application No. 201780004221.8, dated Apr. 21, 2021.
Notice of Deficiencies, Israel Patent Office, Application No. 259443, dated May 11, 2021, English translation.

* cited by examiner

NONDESTRUCTIVE MEASUREMENT APPARATUS

TECHNICAL FIELD

The present invention relates to a nondestructive measurement apparatus for measuring absorbance of a measurement target such as fruit or vegetable nondestructively.

BACKGROUND TECHNIQUE

A nondestructive measurement apparatus for fruit or vegetable, for measuring absorbance of fruit or vegetable nondestructively has been known.

As an example, there is a nondestructive measurement apparatus which measures absorbance by utilizing a transmission light of a near infrared light irradiated and injected into the fruit or vegetable, and obtains a sugar content of the fruit or vegetable as a Brix value, according to the measured absorbance.

This nondestructive measurement apparatus is described as the nondestructive surge content measurement apparatus in Patent Document 1.

PRIOR ART DOCUMENT

Patent Document

Patent Document 1: Japanese Patent Application publication No. 2002-014042

The nondestructive measurement apparatus as described in Patent Document 1 is one that measures the fruit or vegetable after the harvest as a target. Also, the apparatus is of large size, as the absorbance is measured by mounting the harvested fruit or vegetable on a conveyor.

From the producers of the fruit or vegetable, there are demands for an apparatus that can take not only the harvested fruit or vegetable but also the fruit or vegetable in a state of being born on a tree or the like (growing) before the harvest as a target, and that can comprehend the sugar content by measuring absorbance nondestructively, for the purpose of ascertaining the harvest period and the like.

More specifically, there are demands for a nondestructive measurement apparatus that is compact to a level capable of being held in one hand, so that it can be easily used even for the growing fruit or vegetable.

Also, in the case of making the nondestructive measurement apparatus compact to a level capable of being held in one hand, the adoption of LEDs (Light Emitting Diodes) will be considered, from viewpoints of saving space and saving electricity consumption.

In the case of adopting LEDs, there will be a need for a new devise that enables the stable measurement without causing a shortage of the light amount even for the fruit or vegetable with a thick skin.

SUMMARY OF THE INVENTION

Therefore the object of the present invention is to provide a nondestructive measurement apparatus capable of being compact, and capable of measuring absorbance of a measurement target such as fruit or vegetable nondestructively and stably.

According to one aspect of the present invention, there is provided a nondestructive measurement apparatus, comprising:

a casing including a grip portion capable of being held in hand and a measurement portion having a ring shaped abutting portion to be abutted to a measurement target;

a light source group including a plurality of light sources arranged to be separated in a circumferential direction in an interior of the casing;

a ring lens arranged in a ring shape smaller than the abutting portion at an inner portion surrounded by the abutting portion, for emitting lights coming from the light source group to an external of the casing in a ring shape;

a light guide member having one end surface exposed to an inner side of the ring lens and another end surface positioned in the interior of the casing, for emitting lights incident from the one end surface to the external from the another end surface;

photo sensors arranged inside the casing, for detecting lights emitted from the another end surface of the light guide member; and a light intensity processing unit for obtaining absorbance according to detected intensities of the photo sensors.

Preferably, the nondestructive measurement apparatus further comprises a ring shaped relay lens for guiding lights from the light source group to the ring lens, between the light source group and the ring lens.

Preferably, in the nondestructive measurement apparatus, a main optical axis of a ring shaped light emitted from the ring lens is inclined in a direction for reducing a diameter after emitted from the ring lens.

Preferably, in the nondestructive measurement apparatus, the photo sensors includes at least m sets of photo sensors (where m is an integer greater than or equal to 2), and the nondestructive measurement apparatus further comprises band-pass filters, each having a respective one of m types of different wavelengths $\lambda 1$-$\lambda m$ as a central wavelength, between a respective one of the m sets of photo sensors and the another end surface of the light guide member.

Preferably, in the nondestructive measurement apparatus, the light intensity processing unit obtains the absorbance according to the detected intensities respectively corresponding to the wavelengths $\lambda 1$-$\lambda m$ obtained by the m sets of the photo sensors, and calculates a Brix value from the obtained absorbance.

Preferably, in the nondestructive measurement apparatus, the grip portion is formed to be capable of being held in hand by having a handle, and the measurement portion is formed such that an extending direction of the abutting portion is a direction along the handle, at one end portion of the handle in the grip portion, and a tip end surface of the abutting portion is positioned to be protruded from a surface of the grip portion.

Preferably, the nondestructive measurement apparatus further comprises a diffusion unit for diffusing passing lights, between a surface surrounded by the abutting portion in the measurement target and the another end surface of the light guide member, in a state of having the measurement target abutted to the abutting portion.

According to the present invention, it is possible to provide a nondestructive measurement apparatus capable of being compact, and capable of measuring absorbance of a measurement target such as fruit or vegetable nondestructively and stably.

EMBODIMENTS FOR IMPLEMENTING THE INVENTION

The nondestructive measurement apparatus according to the present invention will be described by taking an example of a handy nondestructive saccharimeter 51 (also referred to simply as saccharinity meter 51 in the following) which is its one embodiment. Also, in the following, an embodiment of the nondestructive measurement apparatus that takes the fruit or vegetable as a measurement target will be described, but the measurement target of the nondestructive measurement apparatus is not necessarily limited to the fruit or vegetable.

First, the configuration of the saccharinity meter 51 will be described with references to FIG. 1 to FIG. 4.

Figure 1:
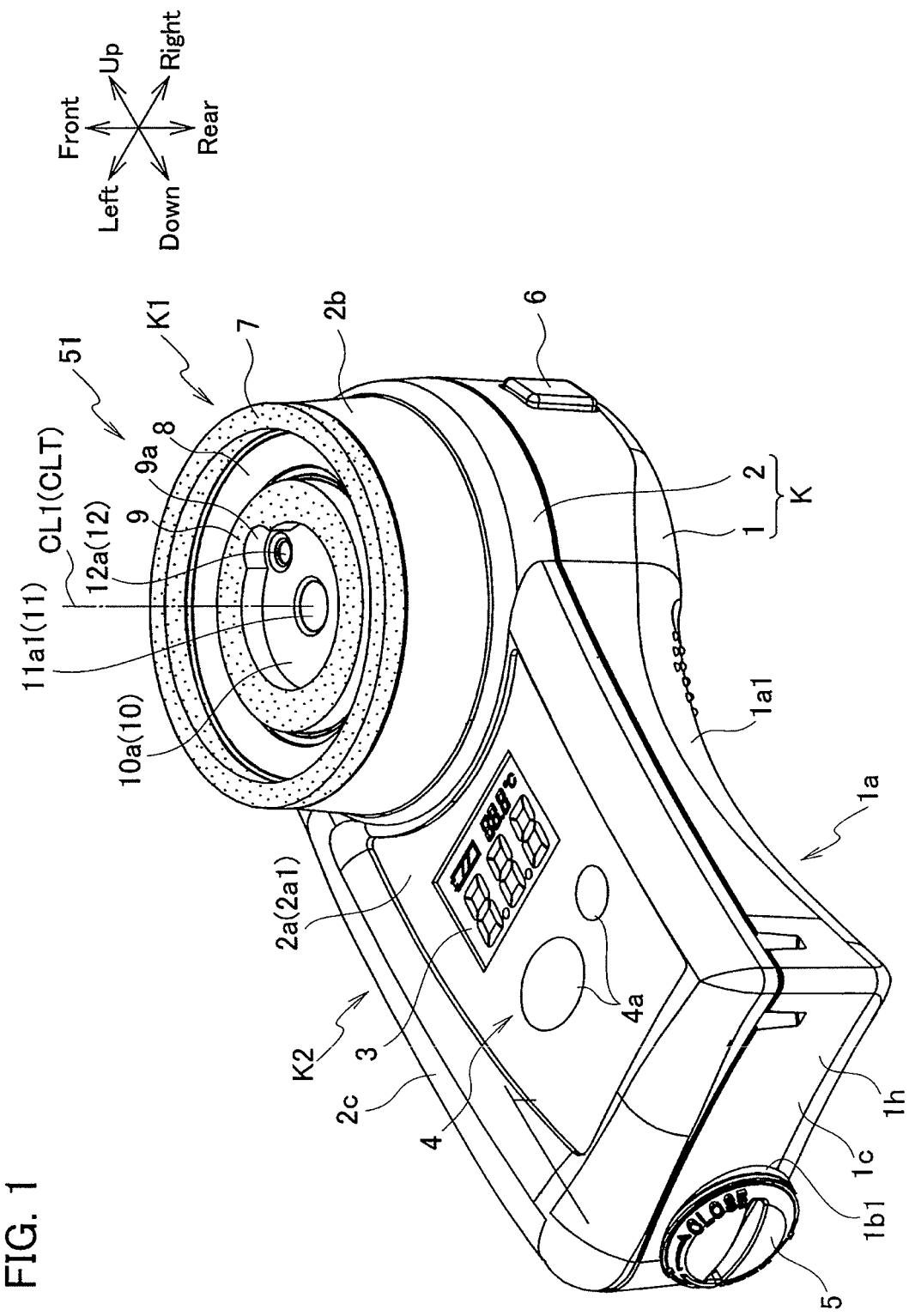
FIG. 1 is a perspective view of an outward appearance of a handy nondestructive saccharimeter 51 (saccharinity meter 51) which is one embodiment of the nondestructive measurement apparatus according to the present invention.
Figure 2:
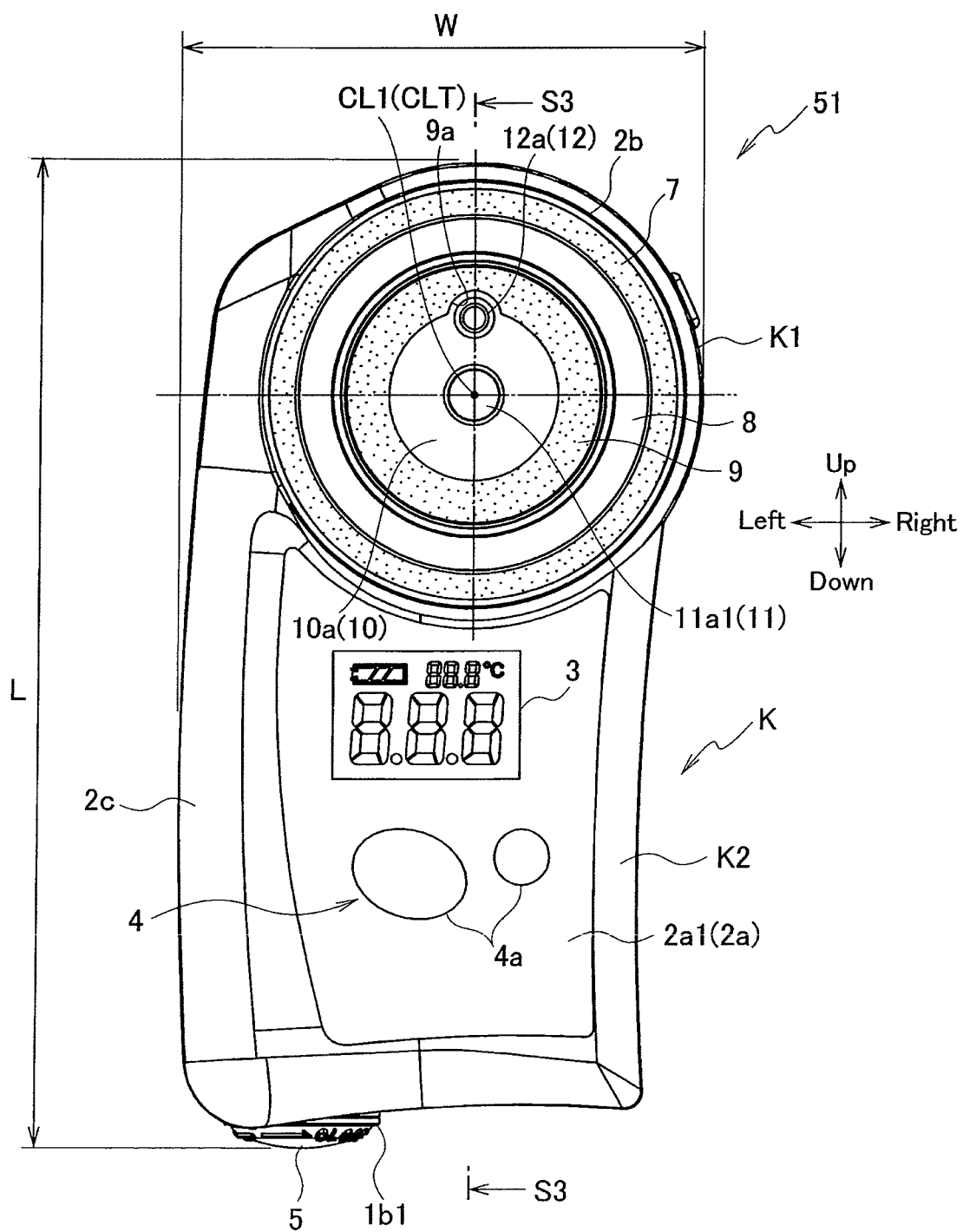
FIG. 2 is a front view of the saccharinity meter 51 of FIG. 1.
Figure 3:
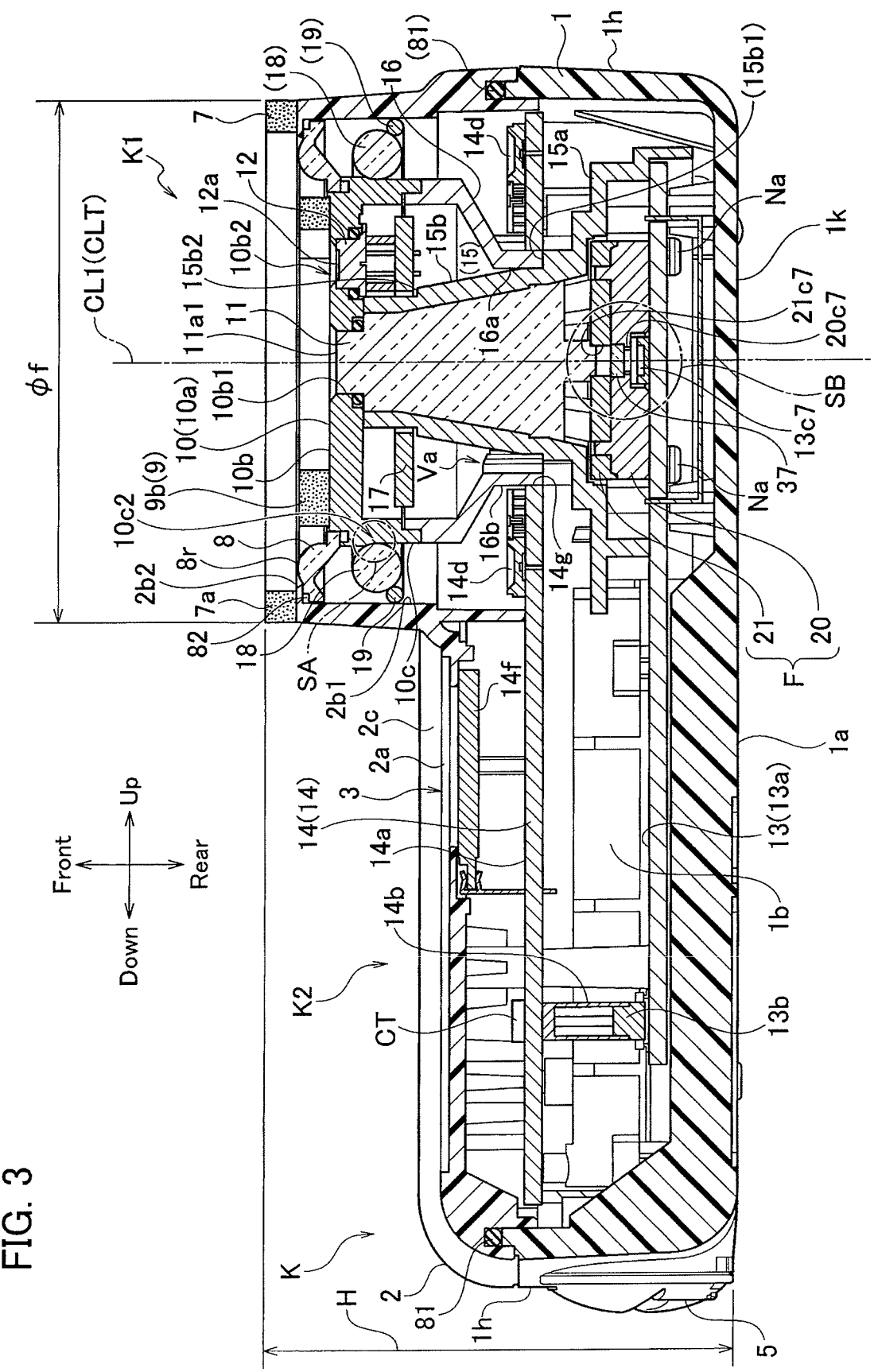
FIG. 3 is a cross sectional view at S3-S3 position in FIG. 2.
Figure 4:
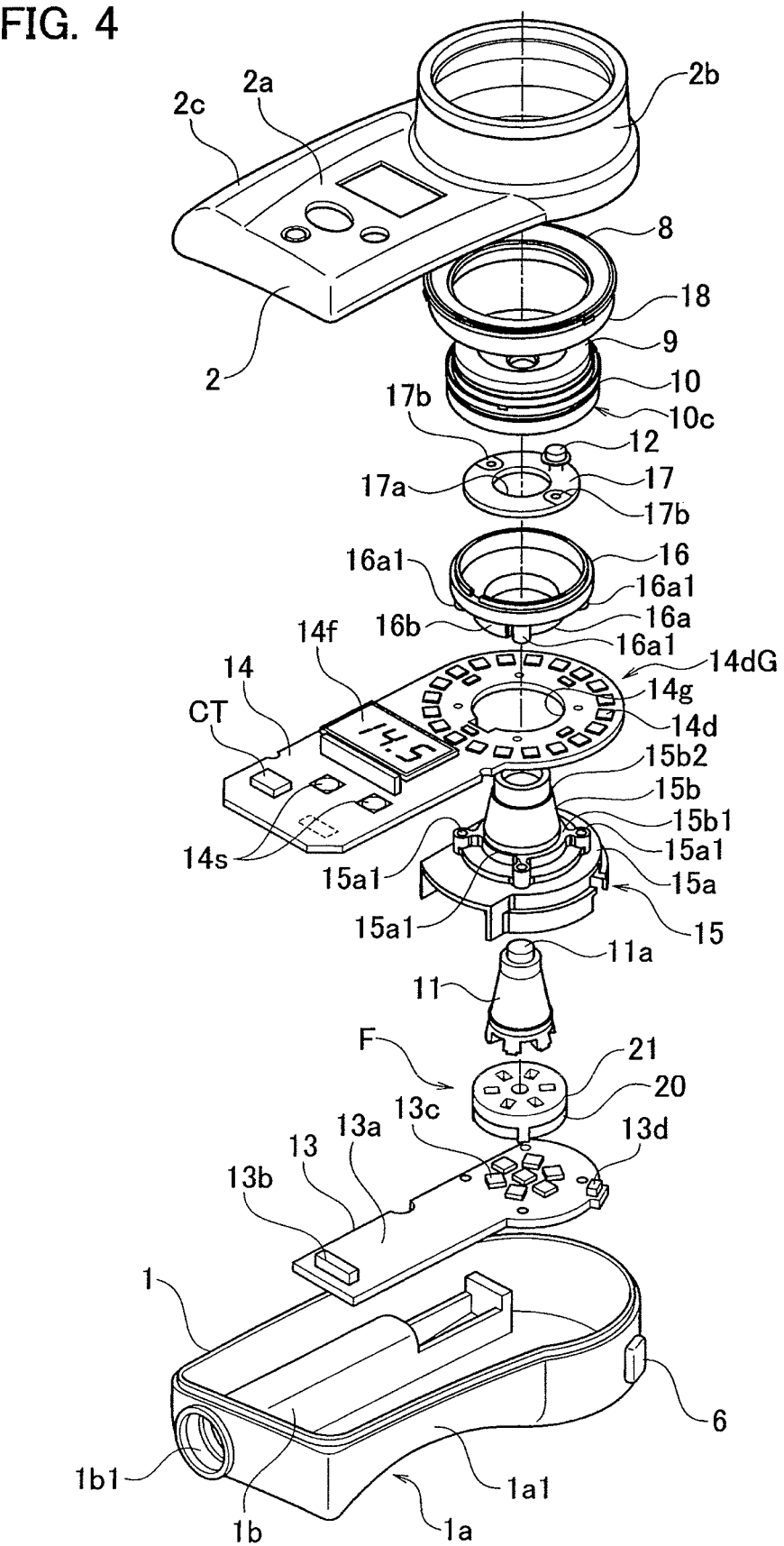
FIG. 4 is an assembly diagram of the saccharinity meter 51 of FIG. 1.

FIG. 1 is a perspective view of an outward appearance of the saccharinity meter 51. FIG. 2 is a front view of the saccharinity meter 51. FIG. 3 is a cross sectional view at S3-S3 position in FIG. 2. FIG. 4 is an assembly diagram of the saccharinity meter 51.

In the following explanation, respective directions of up, down, left, right, front and rear are defined to be directions shown in FIG. 1.

The saccharinity meter 51 is of the so called handy type, which is capable of being held in one hand. Consequently, up, down, left, right, front and rear directions shown in FIG. 1 are defined for the convenience of the explanation, and not limiting a posture and the like of the saccharinity meter 51 at a time of use.

First, an outward appearance configuration of the saccharinity meter 51 will be described.

The saccharinity meter 51 has an approximately box shaped box body 1 with its front side open, and an approximately lid shaped lid body 2 to be attached to the box body 1 so as to close the front side.

As shown in FIG. 3, the box body 1 has a base portion 1k formed to be roughly flat plate shape, and a side wall portion 1h that is erecting in front from a surrounding of the base portion 1k, and is made to be a box shape.

The box body 1 and the lid body 2 constitute a casing K that is integrated with an O-ring 81 (see FIG. 3) mediated in between, by tapping screws not shown in the figure.

The saccharinity meter 51 has the water-proof and dust-proof function of IP65 or above, which is the protection characteristic in the IEC (International Electrotechnical Commission) standard, by the mediation of the O-ring 81 and the other sealing structures not shown in the figure and the like in the casing K.

The casing K has a measurement portion K1 of an approximately cylindrical shape centered around an axial line CL1 extending in the front and rear direction, which is formed on an upper portion, and a grip portion K2 in an approximately flat and rectangular parallelepiped shape extending downward from a rear portion side of the measurement portion K1.

The lid body 2 has a front surface portion 2a having a roughly flat front surface 2a1 in the grip portion K2, and a stage portion 2b protruding forward in a cylindrical shape with respect to a front and rear direction position of the front surface portion 2a in the measurement portion K1.

The lid body 2 has a bank portion 2c protruding forward at a left edge portion of the front surface portion 2a. The bank portion 2c is a portion to be a finger hook in a hand held state to be described below.

The axial line CL1 of the measurement portion K1 is coinciding with a light receiving axial line CLT to be described below.

The light receiving axial line CLT is virtually set up as an optical axis of lights to be received by photo sensors 13c to be described below.

In the grip portion K2, on the front surface 2a1 of the lid body 2, there are provided a display unit 3 for displaying numerals, letters and signs to be visually recognizable by a display element 14f (see FIG. 3 and FIG. 6), and a switch unit 4 containing a plurality of switch pressing portions 4a for selecting an operation mode and zero resetting by pressing with a finger.

Figure 14:
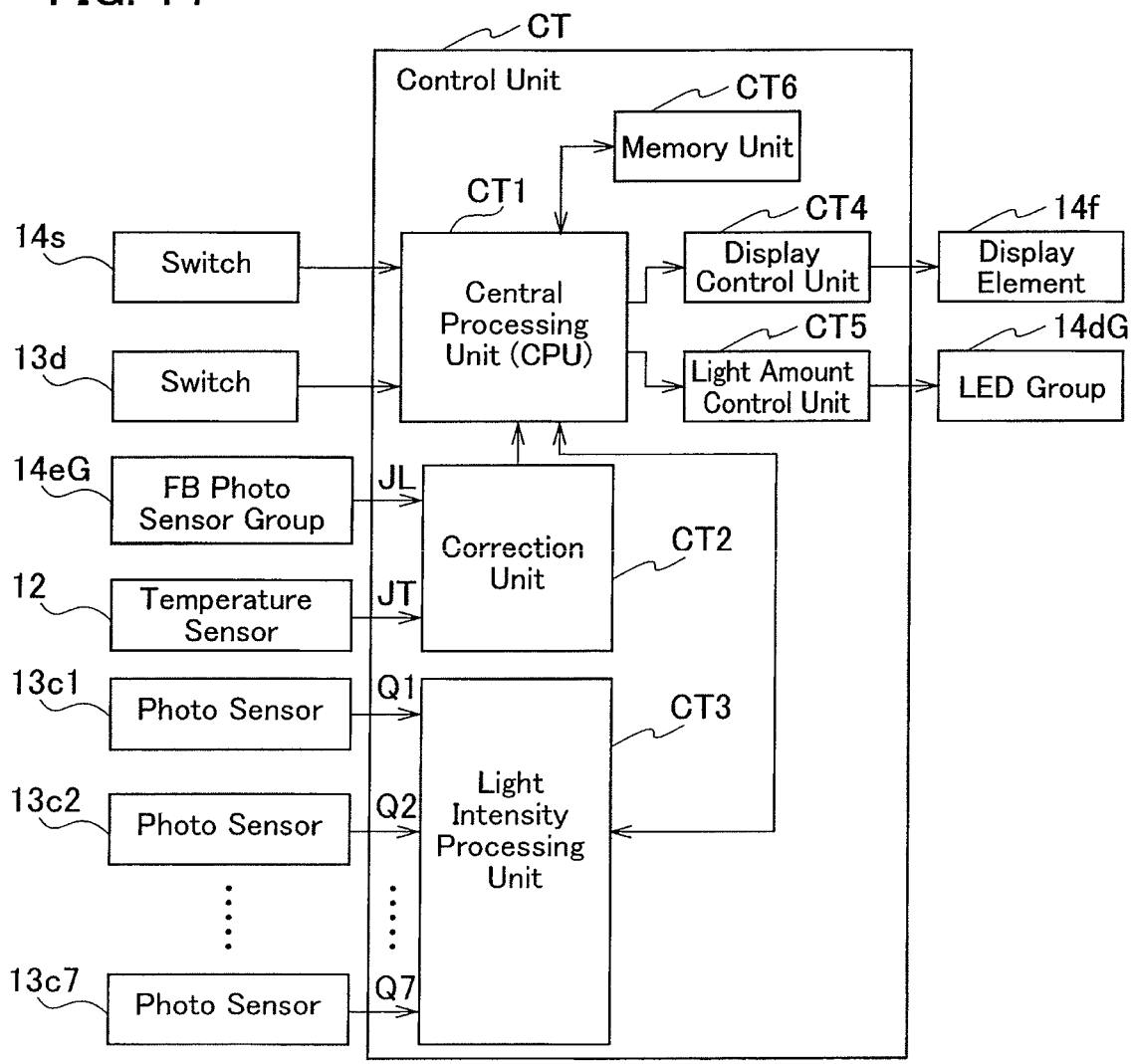
FIG. 14 is a diagram for explaining a control system of the saccharinity meter 51 of FIG. 1.

The display unit 3 displays an operation state of the saccharinity meter 51, a battery remaining amount, and a sugar content (Brix value) obtained by the measurement, for example, under the control of a control unit CT (see FIG. 3 and FIG. 14).

On a left rear portion in the interior of the box body 1, a battery box 1b (see FIG. 3) having an outlet/inlet 1b1 on a lower surface 1c, for accommodating a battery is formed.

To the outlet/inlet 1b1, a battery lid 5 is attached to be freely detachable.

In the battery box 1b, a size AAA battery, for example, is accommodated to be capable of being inserted and removed from the outlet/inlet 1b1 by a user.

On an upper right portion of the box body 1, a press button 6 is provided. Whenever the press button 6 is pressed by the user or the like, a switch 13d (see FIG. 4 and FIG. 5) provided in the interior is activated and operations of start and stop of the measurement are executed alternately.

The grip portion K2 is formed in a size that can be held by one hand of an adult.

At a time of holding the grip portion K2 with a right hand, for example, in order to use this saccharinity meter 51, when a palm is touched to a rear surface 1a of the box body 1, four fingers from an index finger to a little finger will naturally be hooked by the bank portion 2c, so that the user can hold the saccharinity meter 51 well.

In this holding state, the press button 6 is provided at a position that is easy to press by a thumb.

Also, on a right portion of the rear surface 1a of the box body 1, a padding portion 1a1 (see FIG. 1) of a concave curving surface in accordance with a thenar is formed so that a thenar portion of the hand will touch with a good feel.

The box body 1 and the lid body 2 are formed by resin. The resin is a near infrared absorption grade of a black polycarbonate resin, for example.

Next, an outward appearance configuration of the measurement portion K1 will be described in detail.

To a tip end of the stage portion 2b in the lid body 2, a ring shaped outer abutting portion 7 is attached. The outer abutting portion 7 is formed by a material having elasticity with respect to at least a compression to rearward. An example of the material is a sponge.

In the front side view shown in FIG. 2, a ring lens 8 that is a lens member, an inner abutting portion 9, and a part of a front surface 10a of a stage base 10 are visible in respective ring shapes, sequentially from an outer side, in an inner side portion surrounded by the outer abutting portion 7. In a central portion containing the axial line CL1, a front end surface 11a1 of a light guide member 11 is visible.

The inner abutting portion 9 is formed in a ring shape, and attached to the front surface 10a.

The inner abutting portion 9 is formed by a material having elasticity with respect to at least a compression to rearward. An example of the material is a sponge.

The inner abutting portion 9 has a cut out portion 9a carved in an arc shape to outward in a radial direction, at a part of an inner edge.

To the stage base 10, a temperature sensitive surface 12a of a temperature sensor 12 is attached to be exposed to a front side.

The temperature sensor 12 is arranged such that a part of the temperature sensitive surface 12a is entering within the cut out portion 9a, when viewed from a front.

The temperature sensor 12 is the so called thermopile, which measures a temperature T2 in a noncontact manner of a surface of the fruit or vegetable AS (see FIG. 15 and FIG. 16) that is a measurement target put in contact with the measurement portion K1, and measures a temperature T1 corresponding to the casing K in the surrounding as well. The temperature sensor 12 outputs the measured temperature T1 and temperature T2 toward the control unit CT as temperature information JT (see FIG. 14). The temperature T1 and the temperature T2 may be reversed. Namely, the temperature of the surface of the fruit or vegetable AS may be set as the temperature T1.

In the casing K, the measurement portion K1 is integrally formed on one end side (an upper side) of the grip portion K2, in such a posture that an extended surface in a ring shape of the outer abutting portion 7 and the inner abutting portion 9 becomes a surface along the up and down direction that is a length direction of the grip portion K2 (to be roughly parallel, for example).

As shown in FIG. 3, a position in the front and rear direction of each portion in the measurement portion K1 is such that a front end surface 9b of the inner abutting portion 9 is on a rear side, with respect to a front end surface 7a of the outer abutting portion 7.

The ring lens 8 is arranged in the roughly same front and rear position as the inner abutting portion 9.

A front end ridgeline portion 8r positioned at a front-most side in the ring lens 8 is in the roughly same front and rear position as the front end surface 9b of the inner abutting portion 9.

The front surface 10a of the stage base 10 is on a rear side, with respect to the front end surface 9b of the inner abutting portion 9.

The front end surface 11a1 of the light guide member 11 is positioned on the same position in the front and rear direction or on a slightly rear side, with respect to the front surface 10a of the stage base 10.

Next, parts and the like arranged in the interior of the casing K will be described with references to FIG. 3 to FIG. 12.

As shown in FIG. 3 and FIG. 4, in the interior of the casing K, two large substrates are accommodated in parallel, to be facing against each other in the front and rear direction. More specifically, they are a sensor substrate 13 and a base substrate 14 from the base portion 1k side of the box body 1.

Figure 5:
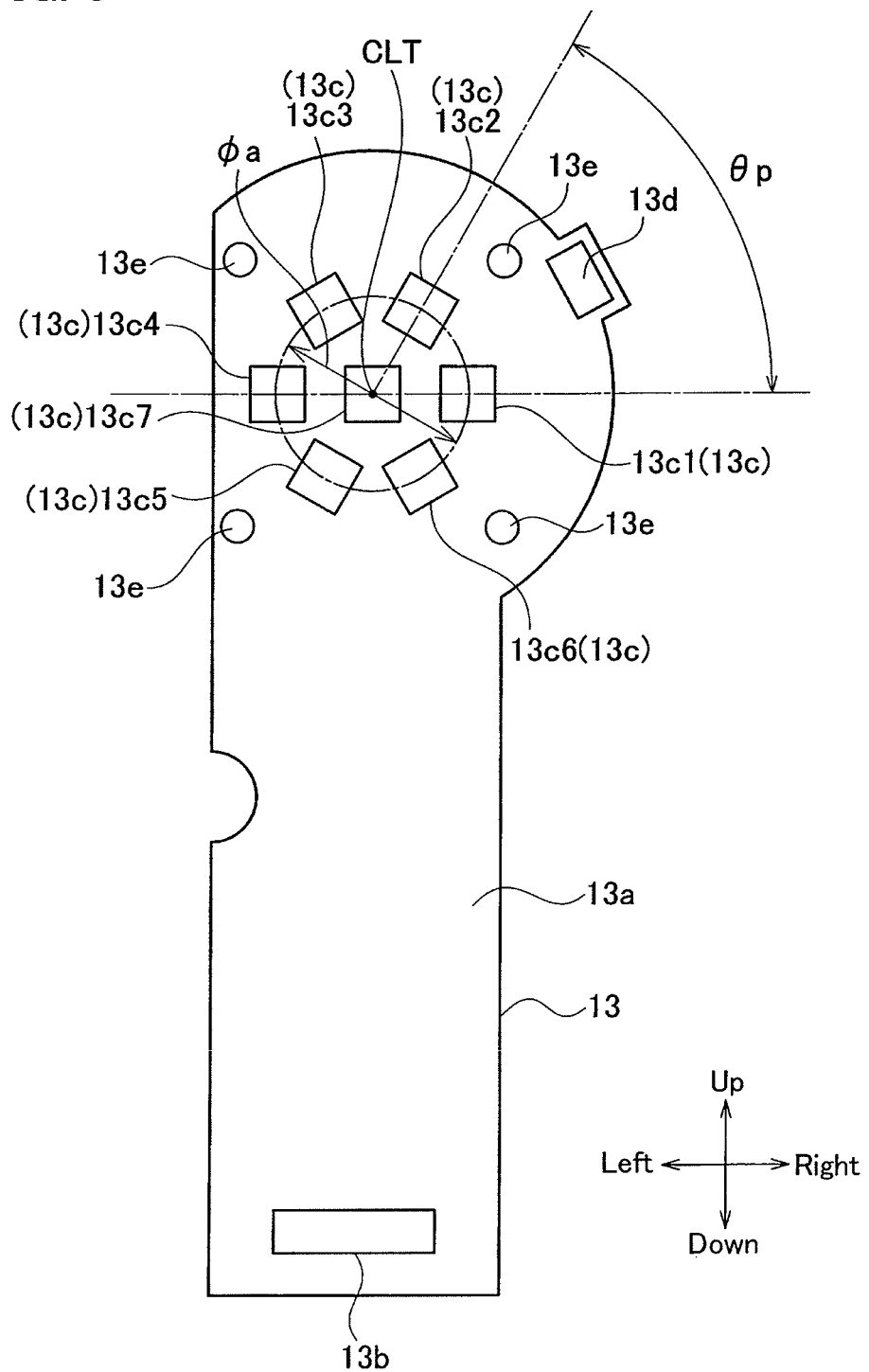
FIG. 5 is a front view of a sensor substrate 13 equipped by the saccharinity meter 51 of FIG. 1.

FIG. 5 is a front view for explaining the sensor substrate 13.

The sensor substrate 13 has a receptacle 13b, a plurality of photo sensors 13c, and a switch 13d implemented on a front surface 13a to be a front side in a state of being accommodated within the casing K.

The receptacle 13b is installed on a plug 14b of the base substrate 14 arranged in front of the sensor substrate 13, such that the sensor substrate 13 and the base substrate 14 are electrically connected (see FIG. 3).

The plurality of photo sensors 13c are provided to be seven in this example. Six of the photo sensors 13c among seven of them are implemented such that they are equally distanced by an angle pitch θp of 60° around the light receiving axial line CLT, such that a central position of each photo sensor 13c is on a line of a diameter φa.

The remaining one is implemented at a central position of the diameter φa.

These seven photo sensors 13c will be distinguished as photo sensors 13c1 to 13c7, as shown in FIG. 5, in the case where a distinction becomes necessary in the later explanation.

The switch 13d alternately repeats an ON operation and an OFF operation whenever the press button 6 is pressed as already described, in the assembled saccharinity meter 51.

The sensor substrate 13 has four piercing holes 13e at approximately 90° interval, at positions on outer side in the diameter direction than the photo sensors 13c.

Figure 6:
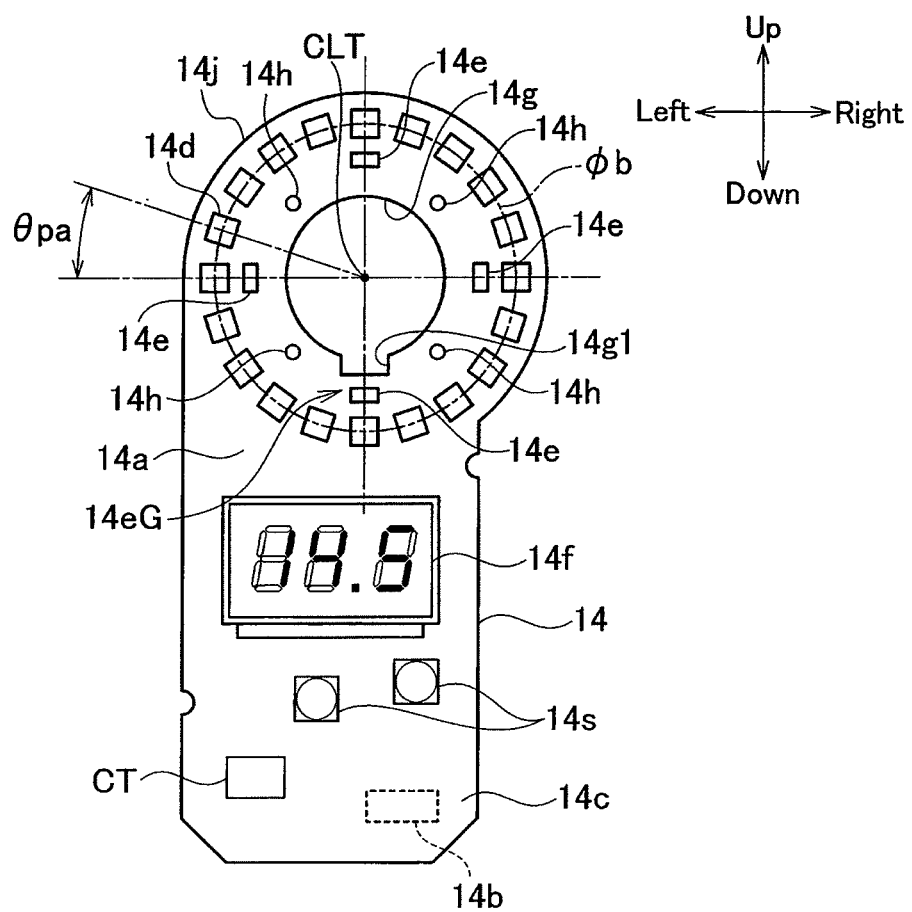
FIG. 6 is a front view of a base substrate 14 equipped by the saccharinity meter 51 of FIG. 1.

FIG. 6 is a front view for explaining the base substrate 14.

The base substrate 14 has a circular hole 14g centered around the light receiving axial line CLT on an upper portion, a cut out portion 14g1 carved in a rectangular shape toward downward, and holes 14h at an outer side of the hole 14g in oblique 45° directions with respect to up, down, left and right, respectively.

The base substrate 14 has an arc portion 14*j* to be an arc shaped outer shape centered around the light receiving axial line CLT.

The base substrate 14 has the display element 14*f*, a switch 14*s*, a plurality (n sets; where n is an integer greater than or equal to 2) of LEDs 14*d* as the light emitting elements to be the light source, a plurality of FB (feedback) photo sensors 14*e*, and the control unit CT for controlling operations of the saccharinity meter 51, implemented on a front surface 14*a* to be a front side in a state of being accommodated within the casing K.

On the other hand, on a rear surface 14*c*, the plug 14*b* to be connected with the receptacle 13*b* of the sensor substrate 13 is implemented.

The display element 14*f* is a display device such as a liquid crystal device, an organic EL (organic Electro-Luminescence) device and the like, for example.

The plurality of LEDs 14*d* are provided to be twenty (n=20) in this example. These 20 LEDs 14*d* are implemented in a posture to be radial, such that they are equally distanced by an angle pitch θpa of 18° on a line of a diameter θb around the hole 14*g* centered around the light receiving axial line CLT.

In detail, the LEDs 14*d* are arranged to be separated in a circumferential direction at positions close to the arc portion 14*j*.

In the following, they are also referred to as a LED group 14*d*G, as a light source group collecting the plurality of LEDs 14*d* together.

The LEDs 14*d* are arranged sequentially in the circumferential direction, using 6 types having the following wavelengths as respective central wavelengths, for example.

Namely, these wavelengths are 880 nm, 900 nm, 950 nm, 980 nm, 1020 nm, and 1064 nm.

In this case, at least three sets of those LEDs 14*d* that have each wavelength as the central wavelength will be arranged in the entire 20 sets. Among them, respectively four sets of those LEDs 14*d* that have 880 nm and 900 nm as respective central wavelengths will be arranged.

The selection of the LEDs 14*d* with respect to 6 types of wavelengths is not limited to this. As another example, it may use the so called 3-wavelength compound LEDs, in which 3 types of LEDs having 3 types of wavelengths as respective central wavelengths are packaged into one, for 3 types of short wavelengths and 3 types of long wavelengths among 6 types of wavelengths.

For example, using the 3-wavelength compound LEDs having 3 types of wavelengths 880, 900, and 950 nm as the central wavelengths, and the 3-wavelength compound LEDs having 3 types of wavelengths 980, 1020, and 1064 nm as the central wavelengths, a total 20 sets including 8 sets of the former and the 12 sets of the latter, for example, may be arranged appropriately.

Between an edge portion of the hole 14*g* and the LEDs 14*d*, the FB (feedback) photo sensors 14*e* (hereafter referred to as the FB photo sensors 14*e*) are implemented in up, down, left and right directions, respectively. In the following, these four FB photo sensors 14*e* will also be referred to collectively as a FB photo sensor group 14*e*G.

As shown in FIG. 3 and FIG. 4, with respect to the sensor substrate 13, a flat cylindrical shaped filter unit F is arranged to cover seven sets of the photo sensors 13*c*.

On a front side of the filter unit F, the light guide member 11 formed to be solid and roughly truncated cone shape is arranged.

The filter unit F and the light guide member 11 are provided on the sensor substrate 13 from a front side, and along with a unit holder 15, sandwiched between the sensor substrate 13 and a stage base mount 16 that is fastened and fixed by tapping screws Na from a rear side. A specific configuration of the light guide member 11, the stage base mount 16, and the filter unit F will be described below.

As shown in FIG. 3 and FIG. 4, the unit holder 15 has a base portion 15*a* in a round pot shape with a rear side open and a front side becoming a bottom, and a protruding portion 15*b* protruding to forward from the base portion 15*a*.

On the base portion 15*a*, four piercing holes 15*a*1 (see FIG. 4) extending in the front and rear direction in order to insert the tapping screws Na are formed, in oblique 45° directions with respect to up, down, left and right.

The protruding portion 15*b* is formed in a hollow cone shape, such that the light guide member 11 can be fit inside almost without any gap, and protruding to forward through the hole 14*g* of the base substrate 14.

On an outer circumferential surface of the protruding portion 15*b*, a step portion 15*b*1 and a step portion 15*b*2 with diameters suddenly changing at two locations on a rear side and a tip end side are formed.

With respect to an inner diameter of the hole 14*g* of the base substrate 14, an outer diameter of the protruding portion 15*b* is set smaller, and a rear end portion 16*a* of the stage base mount 16 is engaged between the hole 14*g* and the protruding portion 15*b*. The rear end portion 16*a* has a front and rear direction position determined by abutting to the step portion 15*b*1 of the protruding portion 15*b*.

The stage base mount 16 is formed in an approximately funnel shape with a tapering rear end portion side.

On the rear end portion 16*a*, a passage portion 16*b* protruding to a lower side is formed.

An outer shape of the passage portion 16*b* is made to be engaged with the cut out portion 14*g*1 in the hole 14*g* of the base substrate 14. Namely, with respect to the base substrate 14, a position is determined around the light receiving axial line CLT of the stage base mount 16.

An inner circumferential surface of the rear end portion 16*a* is abutted to an outer surface of the protruding portion 15*b* of the unit holder 15, except for a portion of the passage portion 16*b*.

Namely, a gap Va (see FIG. 3) is formed between the passage portion 16*b* and the protruding portion 15*b*.

This gap Va will become a passage for passing a lead wire from a temperature sensor substrate 17 to be described below, in the front and rear direction.

On the rear end portion 16*a*, four bosses 16*a*1 extending in front and rear are formed in oblique 45° directions with respect to up, down, left and right in the front view. In each boss 16*a*1, a bottomed hole with a front side as a bottom is formed.

By inserting the tapping screws Na shown in FIG. 3 into the piercing holes 13*e* of the sensor substrate 13 and the piercing holes 15*a*1 of the unit holder 15, and screwing them into the bottomed holes formed in the bosses 16*a*1 of the stage base mount 16, the unit holder 15 and the stage base mount 16 are fixed with respect to the sensor substrate 13.

At that point, the filter unit F and the light guide member 11 are held by being sandwiched between the sensor substrate 13 and the unit holder 15.

In front of the stage base mount 16, the stage base 19 is arranged.

The stage base 10 has a disk shaped stage bottom portion 10*b* (see FIG. 3), and a ring shaped circumferential wall portion 10*c* erecting rearward from a periphery of the stage bottom portion 10*b*. The front surface 10*a* already described is a front surface of the stage bottom portion 10*b*.

As shown in FIG. 3, at a center (a position of the light receiving axial line CLT) of the stage bottom portion 10b, a piercing hole 10b1 is formed. Also, on an upper side with respect to the piercing hole 10b1, a piercing hole 10b2 is formed.

Into the piercing hole 10b1, a tip end portion of the light guide member 11 is entered from a rear side, and the front end surface 11a1 of the light guide member 11 is exposed forward.

Into the piercing hole 10b2, the temperature sensor 12 is entered from a rear side, and the temperature sensitive surface 12a is exposed forward.

In the interior surrounded by the circumferential wall portion 10c of the stage base 10, the temperature sensor substrate 17 is arranged.

As shown in FIG. 4, the temperature sensor substrate 17 is in a disk shape, and formed by hiving a central hole 17a and a pair of piercing holes 17b.

Also, on the temperature sensor substrate 17, the temperature sensor 12 is implemented.

The temperature sensor substrate 17 is attached to the stage bottom portion 10b by the tapping screws (not shown in the figure) piercing through the piercing holes 17b.

From the temperature sensor substrate 17, the lead wire (not shown in the figure) is drawn out rearward, and drawn around to the sensor substrate 13 through the gap Va.

The stage base mount 16 and the stage base 19 are formed by resin. The resin is a near infrared absorption grade of a black polycarbonate resin, for example.

By forming the unit holder 15 with metal, a shielding function is exhibited, so that the influence of disturbance noises with respect to the sensor substrate 13 can be reduced.

Figure 7:
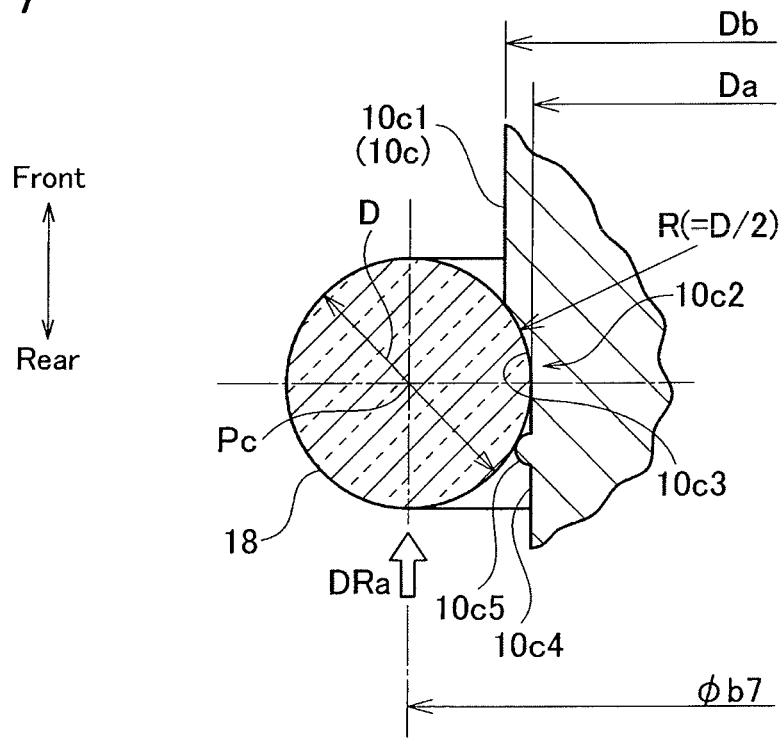
FIG. 7 is a partial cross sectional view for explaining an attaching state of a relay lens 18 equipped by the saccharinity meter 51 of FIG. 1.

To the circumferential wall portion 10c of the stage base 10, a relay lens 18 is attached. Next, the relay lens 18 and its attachment method will be described with reference mainly to FIG. 7. FIG. 7 is an enlarged view of an SA section in FIG. 3.

In FIG. 7, on an outer circumferential surface 10c1 of the circumferential wall portion 10c of the stage base 10, a step unit 10c2 with a slightly larger diameter on a front side is formed around the entire circumference.

The relay lens 18 is attached to the step portion 10c2.

The relay lens 18 is a ring shaped optical member with an inner diameter Da, and a cross sectional shape orthogonal to the extending direction is in a circular shape with a diameter D.

A diameter φb7 of a central position Pc of a ring shaped portion is set to be equal to the diameter φb (see FIG. 6) of the central position of the LED 14d implemented on the base substrate 14.

The relay lens 18 is formed by a transparent polycarbonate resin having an optical transparency, for example.

The outer circumferential surface 10c1 of the circumferential wall portion 10c in the stage base 10 is formed such that an outer diameter on a front side than the step portion 10c2 has a diameter Db which is larger than the inner diameter Da of the relay lens 18.

Then, at the step portion 10c2, it has a diameter that is gradually reduced by a concave curved surface 10c3 of a radius R (=D/2) as one goes rearward, and it is connected to a reduced diameter portion 10c4 having the same outer diameter as the inner diameter Da.

Also, at the reduced diameter portion 10c4, a plurality of minute protrusions 10c5 are formed to be separated by a prescribed interval in the circumferential direction.

The relay lens 18 is attached to be in tight contact with the concave curved surface 10c3 toward a front side, and the minute protrusions 10c5 are regulating a movement of the relay lens 18 to a rear side.

At a time of attaching the relay lens 18 to the step portion 10c2, the relay lens 18 is moved while undergoing the elastic deformation to widen the inner diameter from a rear side (see an arrow DRa), made to get overt the minute protrusions 10c5, and accommodated between the minute protrusions 10c5 and the concave curved surface 10c3.

As shown in FIG. 3, between the relay lens 18 and an inner surface 2b1 of the stage portion 2b in the lid body 2, a seal ring 19 is fitted by a strong fitting.

The seal ring 19 is formed by a spring wire made of metal, for example.

The seal ring 19 is pressing the relay lens 18 against the stage base 10 by the elastic repulsive force of the strong fitting, so that a position of the relay lens 18 is surely maintained without being displaced.

In front of the relay lens 18, the ring lens 8 already described is attached to be facing against the relay lens 18 in the front and rear direction.

The ring lens 8 is formed by a transparent polycarbonate resin having an optical transparency, for example.

Figure 8:
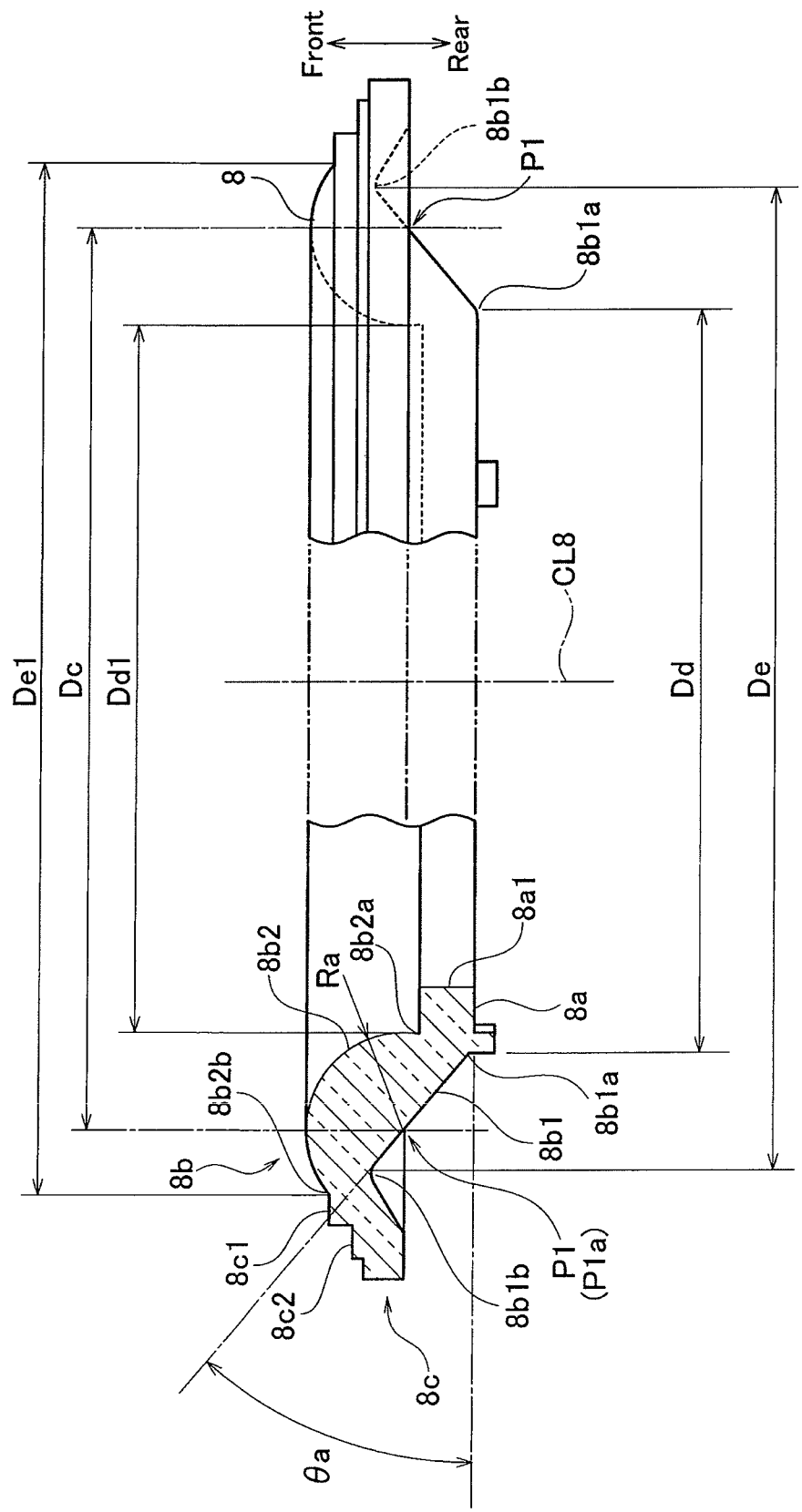
FIG. 8 is a half cross sectional view of a ring lens 8 equipped by the saccharinity meter 51 of FIG. 1.

FIG. 8 is a half cross sectional view (a cross section partially omitted) for explaining the ring lens 8.

As shown in FIG. 8, the ring lens 8 has a ring shaped base portion 8a formed in a ring shape and having a hole 8a1, a deflected portion 8b that is extending out by being inclined forward and outward in the diameter direction from the ring shaped base portion 8a, and a flange portion 8c that is projecting outward in the diameter direction from the deflected portion 8b.

The ring shaped base portion 8a, the deflected portion 8b and the flange portion 8c are formed in a ring shape centered around an axial line CL8 extending from front to rear.

The deflected portion 8b has a light incoming surface 8b1 on a rear side, and a light outgoing surface 8b2 on a front side.

The light incoming surface 8b1 is a conical peripheral surface, passing through a virtual reference circle P1 with a diameter Dc, and inclined at an inclination angle θa toward a front as it goes away from the axial line CL8.

The light outgoing surface 8b2 is formed as a curved surface in which a cross sectional shape shown in FIG. 8 is extending in the circumferential direction with a arc shape in cross section with a radius Ra centered around a point P1a, when an intersection between a plane containing the axial line CL8 and the virtual reference circle P1 is set as the point P1a.

A range in the diameter direction in which the light incoming surface 8b1 is formed is such that an edge portion 8b1a on the inner diameter side has a diameter Dd that is smaller than the diameter Dc, and an edge portion 8b1b on the outer diameter side has a diameter De that is larger than the diameter Dc.

A range in the diameter direction in which the light outgoing surface 8b2 is formed contains at least a range in the diameter direction in which the light incoming surface 8b1 is formed.

More specifically, an edge portion 8b2a on the inner diameter side of the light outgoing surface 8b2 has a diameter Dd1 that is smaller than the diameter Dd, and an edge portion 8b2b on the outer diameter side has a diameter De1 that is larger than the diameter De.

The flange portion 8c has a ring shaped plane portion 8c1 that is connected to the edge portion 8b2b on the outer diameter side of the light outgoing surface 8b2 and orthogonal to the axial line CL8, and a ring shaped shelf portion 8c2 that is formed in a step shape with respect to the plane portion 8c1 and positioned on a rear side, on an outer side in the diameter direction of the plane portion 8c1.

As shown in FIG. 3, the ring lens 8 is attached to close a space between the peripheral portion of the front surface 10a of the stage base 10 and the inner surface 2b1 of the stage portion 2b of the lid body 2.

In detail, the hole 8a1 of the ring shaped base portion 8a engages with the step portion formed on a periphery of the front surface 10a of the stage base 10, to seal with a mediating O-ring (not shown in the figure) and to be fixed by adhesive.

The plane portion 8c1 of the flange portion 8c abuts to a rear surface of an inner flange 2b2 formed to be protruding inward at a tip end of the stage portion 2b, and the O-ring 82 is mediating between its rear surface and the shelf portion 8c2.

Next, the filter unit F will be described with references to FIG. 9 and FIG. 10.

The filter unit F is configured by having a disk shaped filter holder 20, a disk shaped holder cover 21 to be engaged with the filter holder 20 in a direction of an axial line CLf of the filter holder 20, and band-pass filters 31-37 that are a plurality (seven in this example) of optical band-pass filters to be sandwiched between the filter holder 20 and the holder cover 21. For seven band-pass filters 31-37, those having band-pass characteristics in which respective central wavelengths are different and having rectangular outer shapes are adopted.

The filter holder 20 and the holder cover 21 are formed by resin. The resin is a near infrared absorption grade of a black polycarbonate resin, for example.

For the wavelengths to measure the absorbance, m (where m is an integer greater than or equal to 2) types of wavelengths are selected, based on the absorbance wavelengths of the sugar.

In this example, seven types of wavelengths $\lambda 1$-$\lambda 7$ with m=7 are selected. Also, as the photo sensors 13c, m sets of the photo sensors 13c1-13c7 are provided.

Namely, the respective central wavelengths of the band-pass filters 31-37 are set to be wavelengths $\lambda 1$-$\lambda 7$ that are selected and set base on the conventionally known absorbance wavelengths of the sugar.

Also, for the LEDs 14d, those having the emission central wavelengths corresponding to the central wavelengths $\lambda 1$-$\lambda 7$ respectively are selected.

In detail, for the LEDs 14d, those having the emission central wavelengths that are equal to or close to the central wavelengths $\lambda 1$-$\lambda 7$ respectively are selected.

The central wavelengths $\lambda 1$-$\lambda 7$ selected and set in this example are as follows. Also, the wavelengths in parentheses are the emission central wavelengths of the LEDs 14d selected and used in correspondence to the band-pass filters 31-37 respectively.

Band-pass filter 31 . . . $\lambda 1$: 875 nm (880 nm)
Band-pass filter 32 . . . $\lambda 2$: 900 nm (900 nm)
Band-pass filter 33 . . . $\lambda 3$: 950 nm (950 nm)
Band-pass filter 34 . . . $\lambda 4$: 980 nm (980 nm)
Band-pass filter 35 . . . $\lambda 5$: 1020 nm (1020 nm)
Band-pass filter 36 . . . $\lambda 6$: 1050 nm (1064 nm)
Band-pass filter 37 . . . $\lambda 7$: 1064 nm (1064 nm)

In the above noted example, the central wavelengths of the band-pass filters 32-35 and 37 other than the band-pass filters 31 and 36 are coinciding with the emission central wavelengths of the LEDs 14d used in correspondence respectively. Also, differences between the central wavelengths of the band-pass filters 31 and 36 and the emission central wavelengths of the corresponding LEDs 14d are 5 nm and 14 nm, respectively.

With the wavelength difference of this level (less than or equal to 20 nm, for example), no considerable difference in the optical intensity for the respective central wavelengths of the band-pass filters will occur in the generally used LED emission spectrum.

Because the emission spectrum is narrow for the general LED, it is preferable to select a LED having the emission central wavelength corresponding to the central wavelength of the band-pass filter.

On the other hand, in the case of selecting a LED with a low electricity consumption for which the emission spectrum for high luminance is broad, it may not be necessary to select one having the emission central wavelength close to the central wavelength of the band-pass filter.

Figure 9:
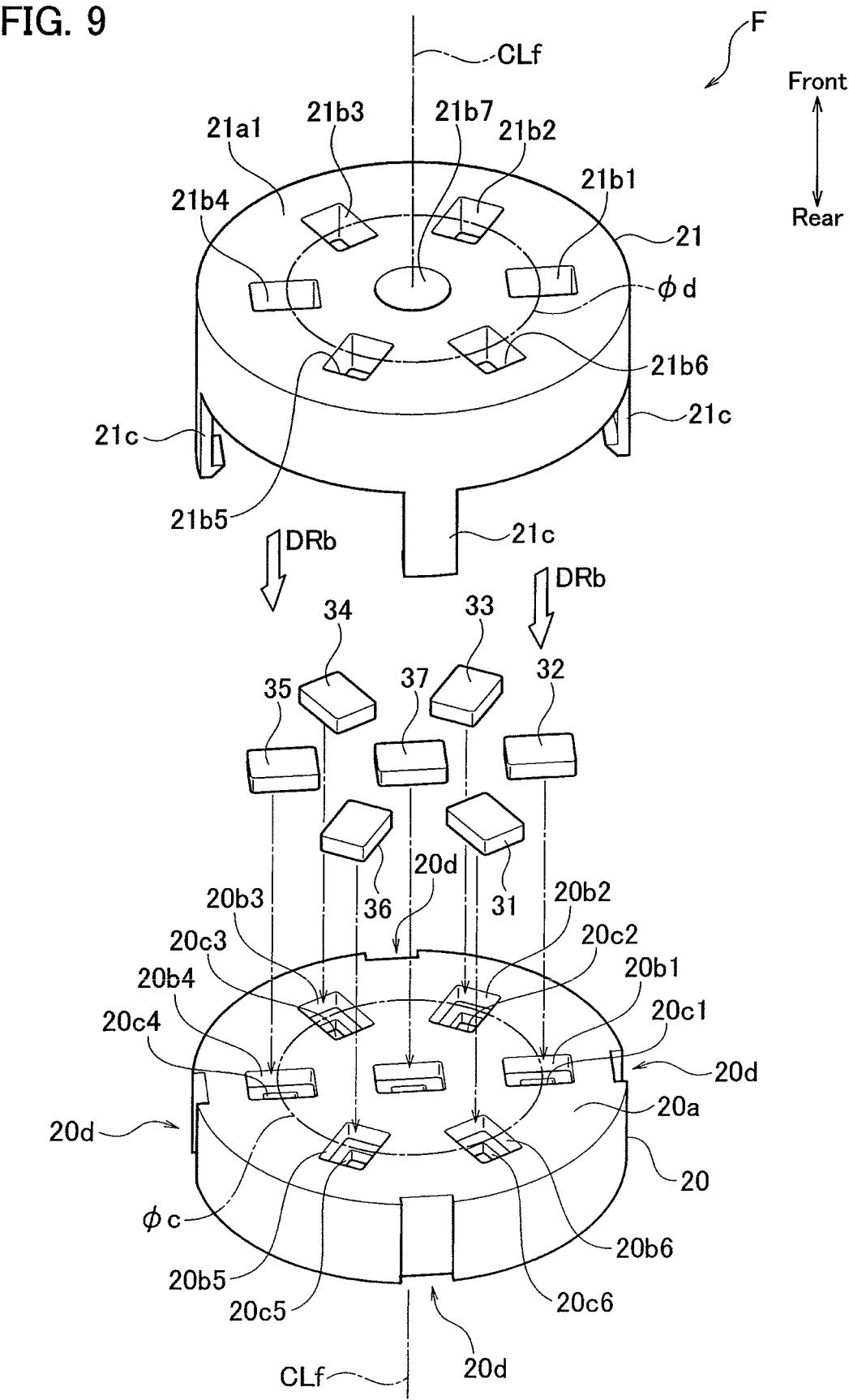
FIG. 9 is an assembly diagram for explaining a filter unit F equipped by the saccharinity meter 51 of FIG. 1.

FIG. 9 is a schematic assembly diagram of the filter unit F.

The filter holder 20 is formed in a disk shape centered around the axial line CLf, and six concave portions 20b1-20b6 formed at an angle pitch of 60° around the axial line CLf with a circle of a diameter $\phi c$ centered around the axial line CLf as a central position and a concave portion 20b7 formed at a center are formed on a front surface 20a. The concave portions 20b1-20b7 are made to be rectangular depressions corresponding to the outer shapes of the band-pass filters 31-37.

The holder cover 21 has a base portion 21a formed in a disk shape, and four claw portions 21c extending out rearward from a peripheral portion of the base portion 21a and to be engaged with the filter holder 20. The claw portions 21c are arranged to be separated by an angle pitch of 90° in the circumferential direction.

On the base portion 21a, rectangular piercing holes 21b1-21b6 are formed at positions with an angle pitch of 60° centered around the axial line CLf and a circle of a diameter $\phi d$ as a center in the diameter direction.

Also, at the central position, a circular piercing hole 21b7 is formed.

The diameter $\phi d$ is set equal to the diameter $\phi c$.

The holder cover 21 can be integrated with the filter holder 20, by approaching close to the filter holder 20 from a front side (see an arrow DRb) and engaging the claw portions 21c with engagement portions 20d provided on the filter holder 20.

Namely, the filter unit F holding the band-pass filters 31-37 is formed by accommodating the respective band-pass filters 31-37 in the concave portions 20b1-20b7 of the filter holder 20, and engaging the holder cover 21 with the filter holder 20 from a front side.

Figure 10:
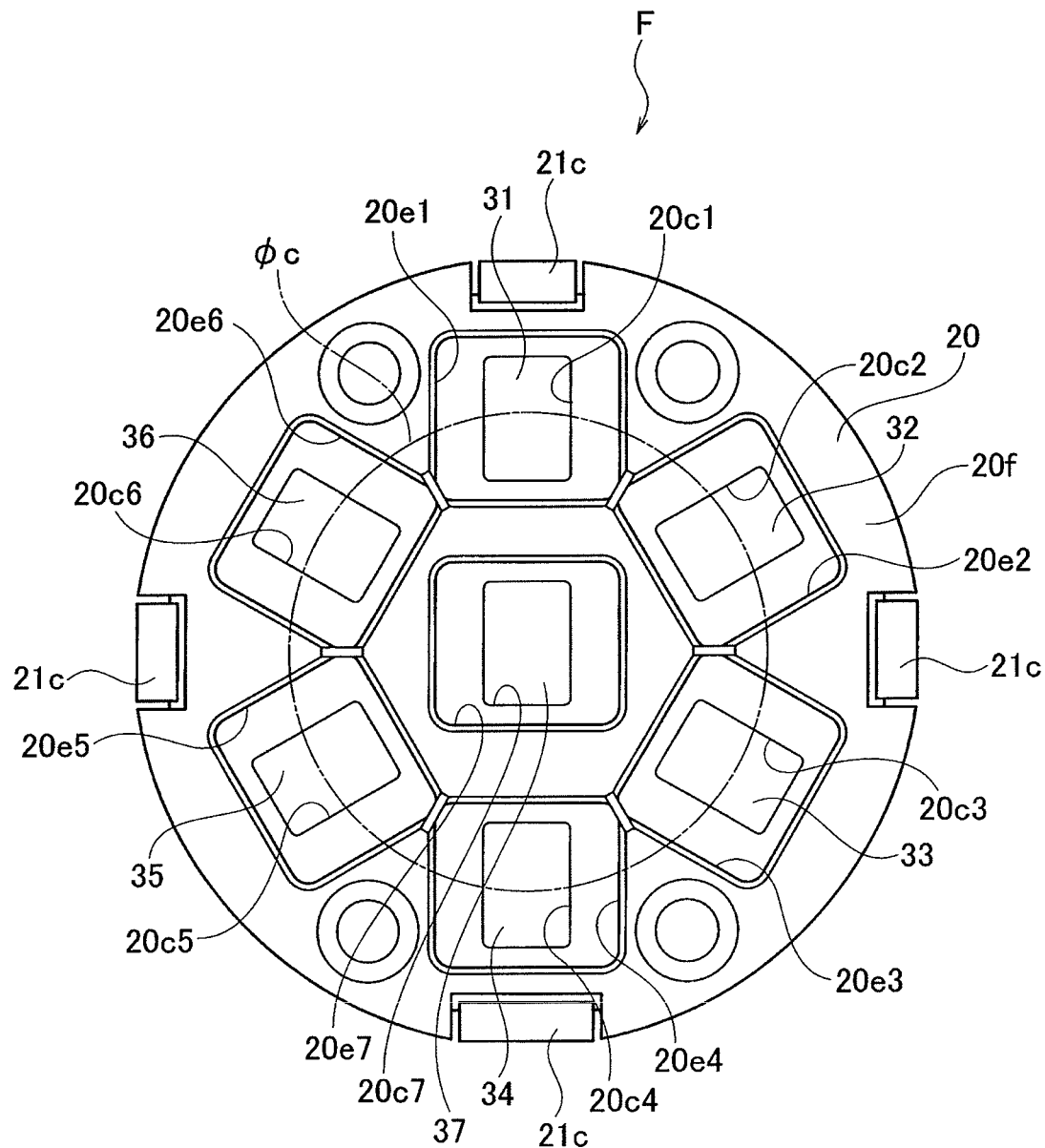
FIG. 10 is a rear view of the filter unit F of FIG. 9.

FIG. 10 is a rear view of the filter unit F.

On a rear surface 20f of the filter holder 20, pocket portions 20e1-20e7 with rectangular openings oriented to a front are formed at positions corresponding to the concave portions 20b1-20b7 formed on the front surface 20a.

The concave portions 20b1-20b7 and the pocket portions 20e1-20e7 are coupled in the front and rear direction by the respective rectangular piercing holes 20c1-20c7. The central position in the diameter direction of the piercing holes 20c1-20c6 is on a circle with the diameter $\phi c$.

Next, the light guide member 11 will be described with references to FIG. 11 and FIG. 12.

Figure 11:
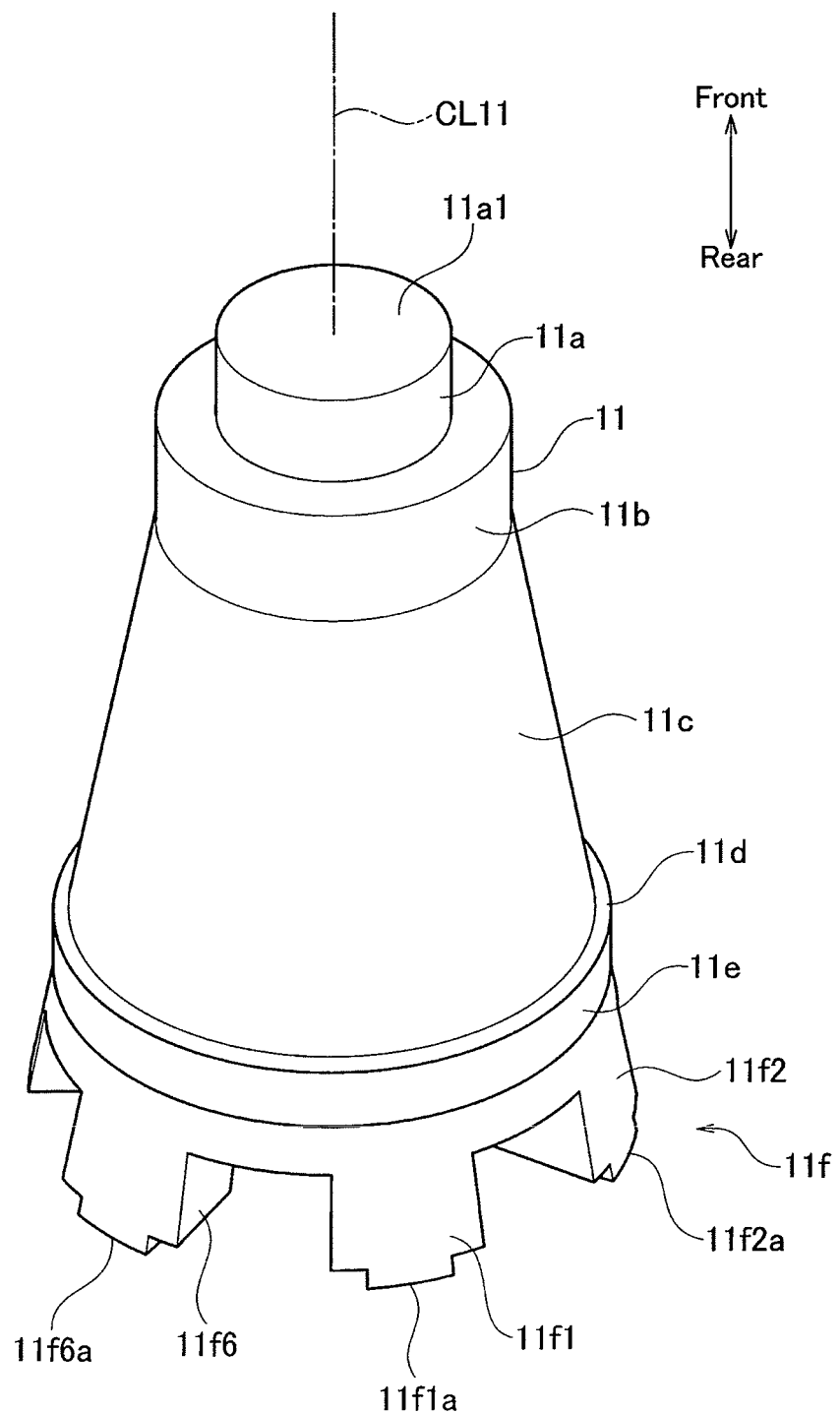
FIG. 11 is a perspective view of a light guide member 11 equipped by the saccharinity meter 51 of FIG. 1.
Figure 12:
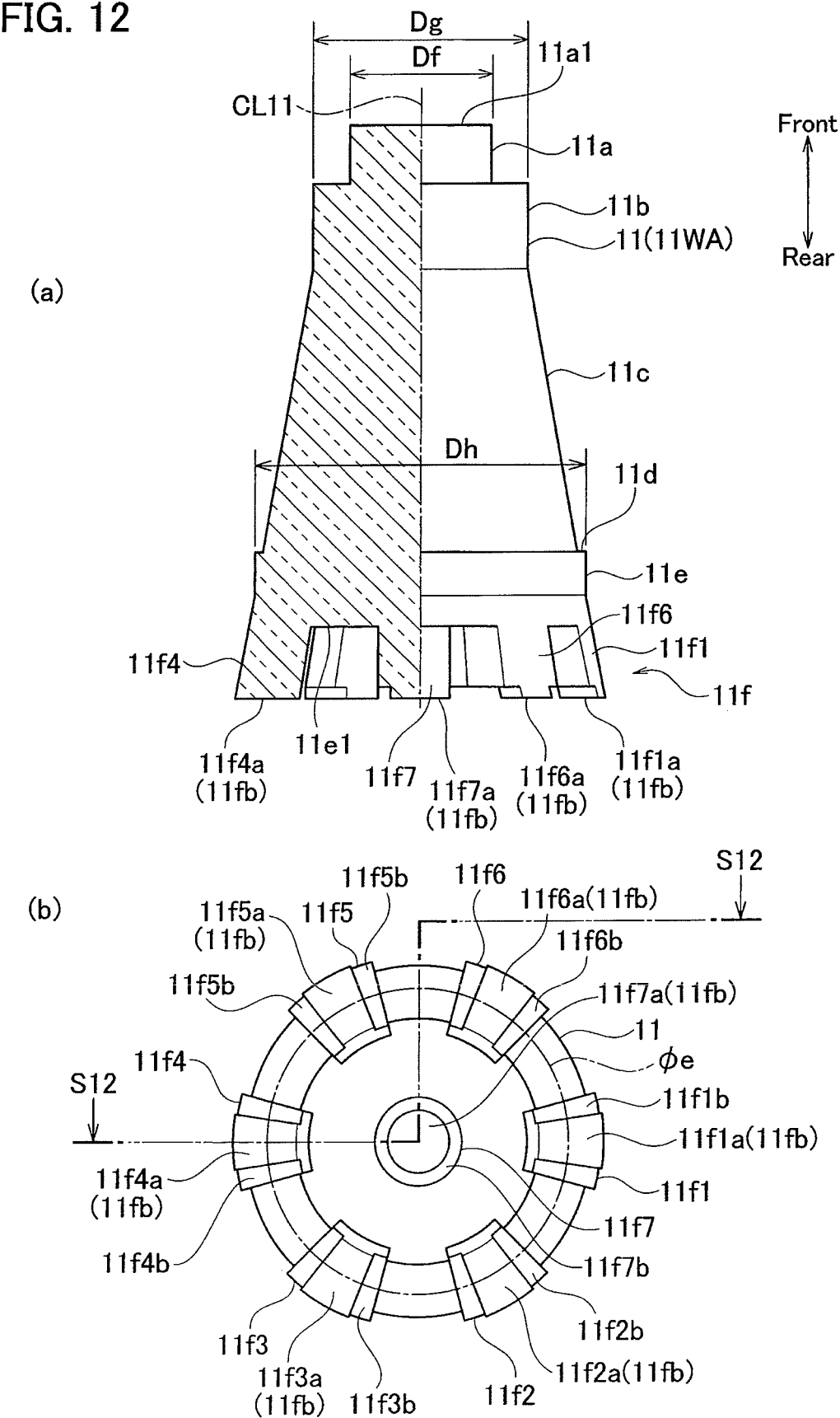
FIG. 12 shows two views of the light guide member 11 of FIG. 11, where (a) is a half cross sectional side view and (b) is a rear view.

FIG. 11 is a perspective view looking at the light guide member 11 from an oblique front FIG. 12 is a half cross sectional view (a) and a rear view (b) of the light guide member 11, FIG. 12(a) is a half cross section at S12-S12 position in the rear view (b).

The light guide member 11 is formed as a transparent member having an optical transparency. A material is a transparent polycarbonate resin having an optical transparency, for example.

The light guide member 11 is formed to be long from front to rear. The light guide member 11 has a front end surface 11a1 as one end surface of its length, and is equipped with a front protruding portion 11a in a cylindrical shape with a diameter Df centered around an axial line CL11 extending from front to rear, an intermediate cylinder portion 11b in a cylindrical shape with a diameter Dg that is larger than the diameter Df, and a truncated cone portion 11c connected to a rear side of the intermediate cylinder portion 11b and having a gradually enlarging diameter as it goes toward a rear.

Moreover, the light guide member 11 is equipped with a rear cylinder portion 11e to be in a cylindrical shape with a diameter Dh via a step portion 11d that has an enlarged diameter in a direction orthogonal with respect to the axial line CL11, and a leg portion 11f having seven light guide protrusion portions 11f1-11f7 formed to be protruding independently toward a rear, from a rear surface 11e1 of the rear cylinder portion 11e.

Six light guide protrusion portions 11f1-11f6 are formed on a circle with a diameter ϕe, with an equal angle interval (at an angle pitch of 60°) centered around the axial line CL11.

The remaining one light guide protrusion portion 11f7 is formed in a column shape at a central position.

Also, the light guide protrusion portions 11f1-11f6 have engagement portions 11f1a-11f6a protruding to a rear further with a reduced diameter in stepped portions 11f1b-11f6b at rear tip end portions.

Also, the light guide protrusion portion 11f7 has an engagement portion 11f7a protruding to a rear further with a reduced diameter in a stepped portion 11f7b at a rear tip end portion.

The positions of the stepped portions 11f1b-11f7b of the engagement portions 11f1a-11f7a and the front and rear direction positions of the tip end portions are set to be the same positions with each other respectively.

The engagement portions 11f1a-11f7a have the stepped portions abutted to the front surface of the base portion 21a of the holder cover 21, and made to enter into the piercing holes 21b1-21b7 of the holder cover 21 in the filter unit F from a front side.

The attachment state of the filter unit F and the light guide member 11 with respect to the sensor substrate 13 will be described with reference to FIG. 13, This attachment is done, as described above, as the filter unit F and the light guide member 11 are sandwiched in the front and rear direction, between the stage base mount 16 and the sensor substrate 13, by fixing the stage base mount 16 with the tapping screws Na.

Figure 13:
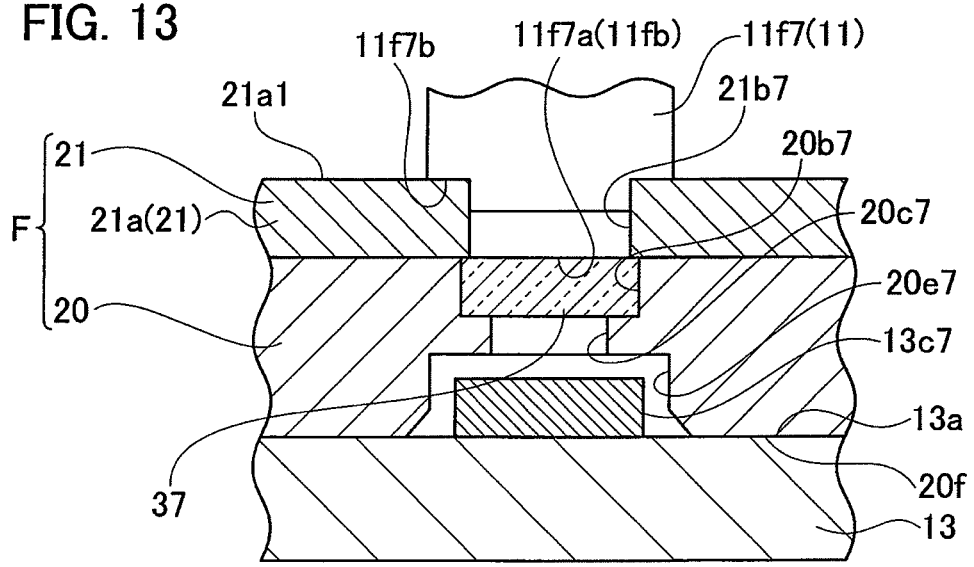
FIG. 13 is an enlarged cross sectional view of a SB section in FIG. 3.

FIG. 13 is a schematic cross sectional view of a SB section in FIG. 3. Namely, it shows the attachment state of the photo sensor 13c7 of the sensor substrate 13, the filter unit F, and the light guide protrusion unit 11f7 in the light guide member 11. It is similar for the other photo sensors 13c1-13c6, and it will be described as a representative example.

As shown in FIG. 13, to the front surface 13a of the sensor substrate 13, the rear surface 20f of the filter holder 20 is abutted.

The photo sensor 13c7 implemented on the front surface 13a is entering into the pocket portion 20e7 formed on the filter holder 20 of the filter unit F.

In the concave portion 20b7 of the filter holder 20, the band-pass filter 37 is inserted. The movement of the band-pass filter 37 toward a front is regulated by being pressed by the piercing hole 21b7 of the holder cover 21 that is formed to be smaller than the outer shape of the band-pass filter 37.

The band-pass filter 37 is in an opposing position in front of the photo sensor 13c7.

In the piercing hole 21b7 of the holder cover 21, the engagement portion 11f7a of the light guide protrusion portion 11f7 of the light guide member 11 is entered and engaged from a front side. The stepped portion 11f7b of the light guide protrusion portion 11f7 is abutted to the front surface 21a1 of the base portion 21a of the holder cover 21.

The operation of the saccharinity meter 51 with the above described configuration is controlled by the control unit CT.

FIG. 14 is a diagram for explaining a configuration of a control system in the saccharinity meter 51.

The control unit CT has a central processing unit (CPU) CT1, a correction unit CT2, a light intensity processing unit CT3, a display control unit CP4, a light amount control unit CT5, and a memory unit CT6

A length L and a width W (see FIG. 2) and a thickness H (see FIG. 3), that are the outer dimensions of the saccharinity meter 51, are set roughly as follows, for example.

$L$=113 mm, $W$=63 mm, $H$=43 mm

Also, the outer diameter ϕf (see FIG. 3) of the measurement portion K1 is set to be 48 mm, for example.

Next, the operation of the saccharinity meter 51 with the above described configuration will be described.

First, the operator brings the measurement portion K1 of the saccharinity meter 51 into contact with the fruit or vegetable AS that is a measurement target.

Figure 15:
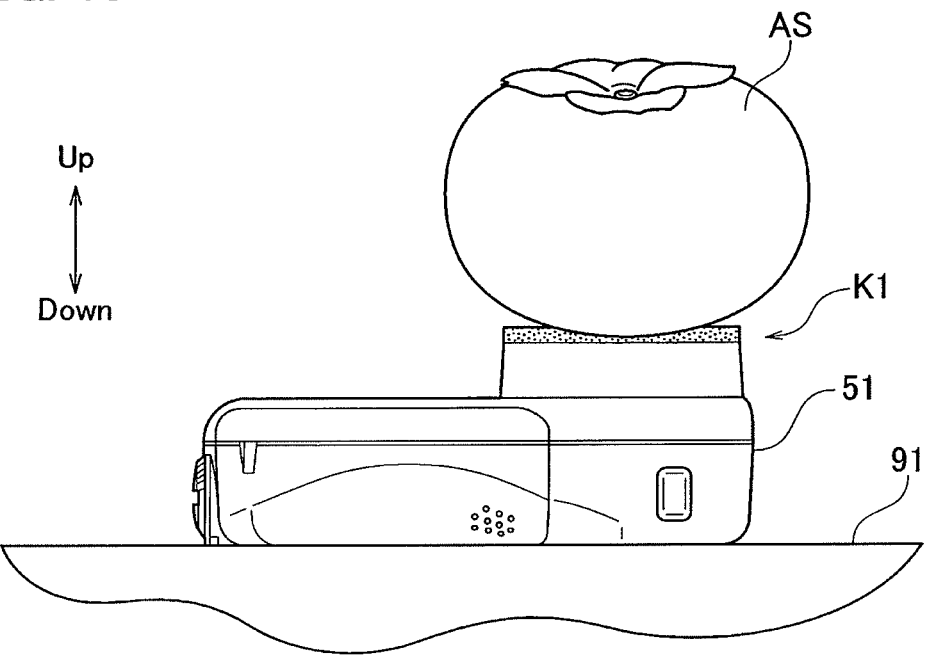
FIG. 15 is a diagram for explaining a manner of measurement by the saccharinity meter 51 of FIG. 1 by mounting on top of table.

More specifically, in the case of measuring the fruit or vegetable AS after the harvest, for example, the operator can make the measurement by mounting the saccharinity meter 51 on a mount such as a table 91, in such an orientation that the outer abutting portion 7 and the inner abutting portion 9 of the measurement portion K1 become an upper end, and mounting the fruit or vegetable AS on the measurement portion K1, as shown in FIG. 15. In the case of measuring the fruit or vegetable AS with a depression in this measurement manner, it is advisable to mount a portion without a depression or a portion with less depression on the measurement portion K1.

Figure 16:
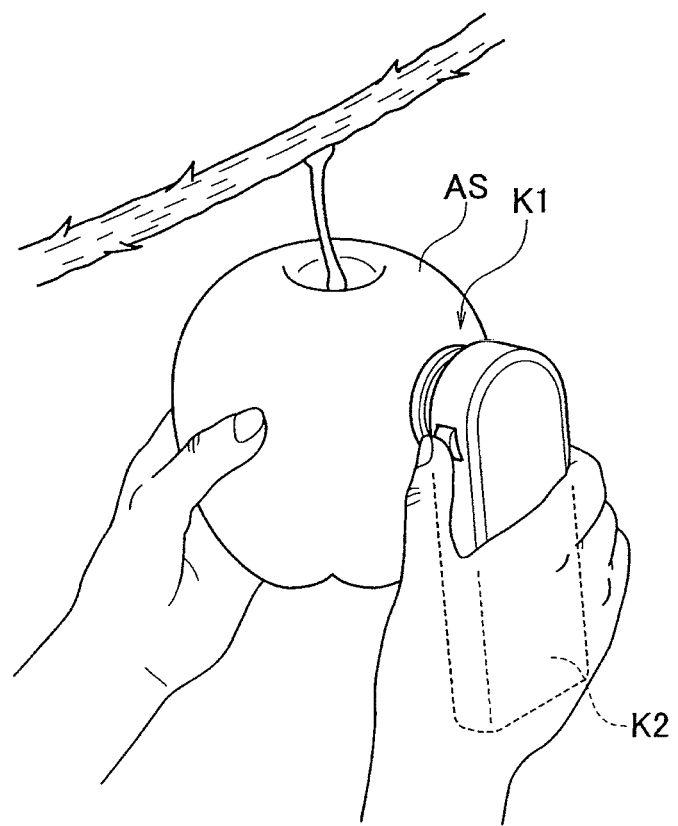
FIG. 16 is a diagram for explaining a manner of measurement by the saccharinity meter 51 of FIG. 1 by being held in hand.

In the case of measuring the fruit or vegetable AS that is before the harvest and still growing, or the fruit or vegetable AS that is heavy or large, the operator holds the grip portion K2 and makes the measurement by bringing the measurement portion K1 into contact with a surface of the fruit or vegetable AS, as shown in FIG. 16.

The measurement portion K1 is formed to be protruding with respect to the grip portion K2.

By means of this, when the saccharinity meter 51 is mounted on a mount and the fruit or vegetable AS is mounted on the measurement portion K1, the convex portions of the uneven surface of the fruit or vegetable AS will abut to the grip portion K2, so that the fruit or vegetable AS will not be mounted unstably.

Also, in the case of making the measurement by holding the saccharinity meter 51 and abutting the measurement portion K1 to the fruit or vegetable AS, it becomes harder for the holding fingers to abut to the fruit or vegetable AS. For this reason, there is a little possibility for the measurement precision to be lowered as a gap between the outer abutting portion 7 and the inner abutting portion 9 and the fruit or vegetable AS is generated and an external light enters.

Figure 17:
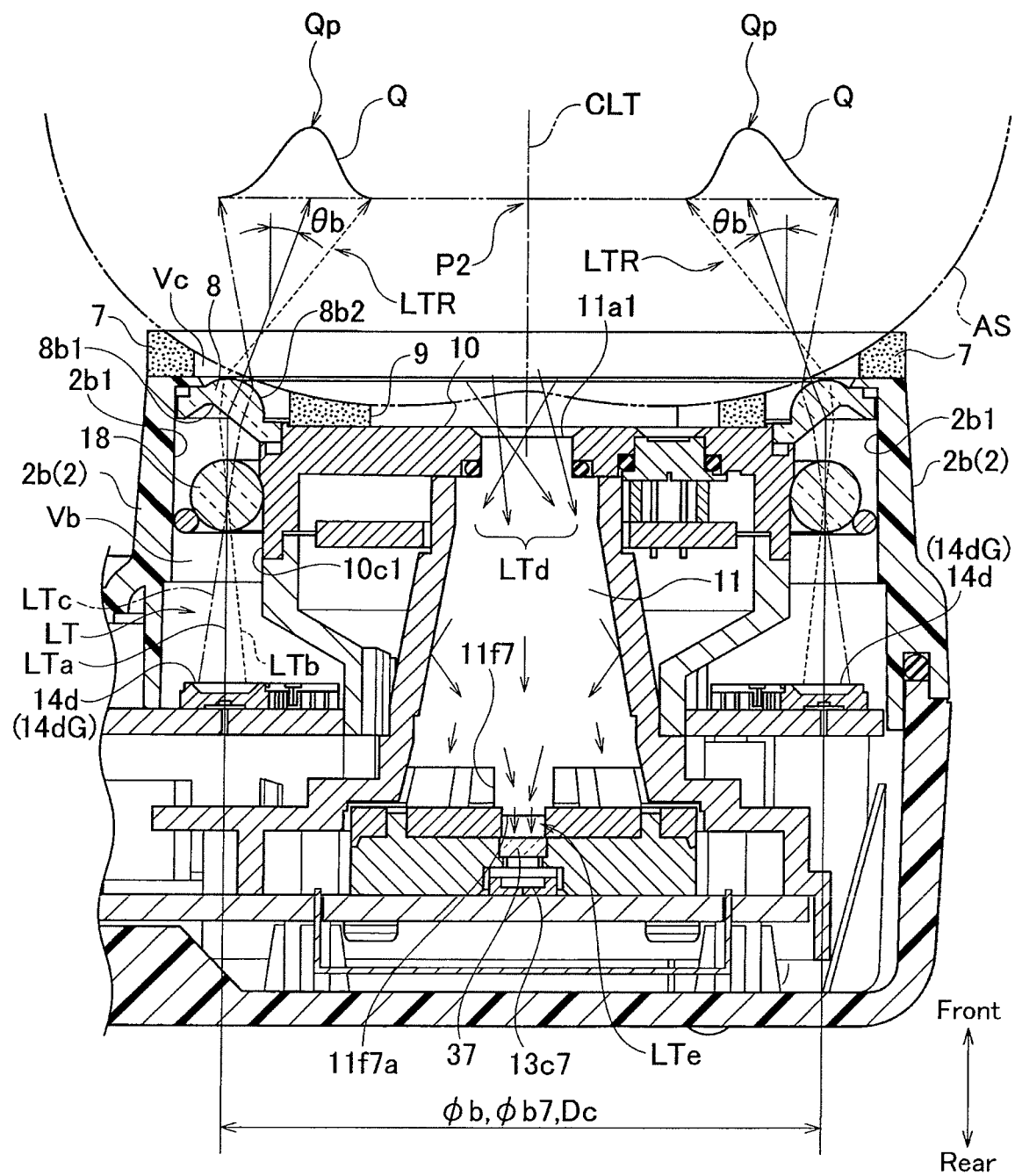
FIG. 17 is a partial cross sectional view for explaining light passages in the saccharinity meter 51 of FIG. 1.

Next, the specific measurement operation of the saccharinity meter 51 will be described with references mainly to FIG. 14 and FIG. 17. FIG. 17 is a schematic diagram for explaining optical paths at a time of making the sugar content measurement by the saccharinity meter 51, which utilizes a portion of the measurement portion K1 of FIG. 3. Also, in FIG. 17, the shading is not depicted for the light guide member 11 that is shown in cross section, so as not to make the drawing too cumbersome.

First, the diameter ϕb (see also FIG. 6) at which the LEDs 14d are arranged to be separated in the circumferential direction, the diameter ϕb7 (see FIG. 7) at a center of the relay lens 18, and the diameter De (see FIG. 8) of the virtual reference circle P1 of the ring lens 8 are set to be equal. The diameter ϕb (=ϕb7−Dc) is set to be a diameter of 38 mm, for example.

(1) The user mounts the fruit or vegetable AS to be measured on the outer abutting portion 7 and the inner abutting portion 9 of the measurement portion K1 of the saccharinity meter 51, in a state of turning on the power of the saccharinity meter 51. Else, the measurement portion K1 of the saccharinity meter 51 is pressed to be in tight contact with the fruit or vegetable AS to be measured.

The fruit or vegetable AS is a fruit or a vegetable that can be tomato, apple, watermelon, and the like.

The outer abutting portion 7 and the inner abutting portion 9 are roughly in tight contact with the surface of the fruit or vegetable AS while being compressed, due to the weight of the fruit or vegetable AS or the pressing force of the user.

(2) The user presses the press button 6, to turn the switch 13d to the ON state. A signal indicating that it is turned to the ON state is send out from the switch 13s to the central processing unit CT1 of the control unit CT.

(3) When it comprehends that the switch 13d is turned to the ON state, the central processing unit CT1 commands the light amount control unit CT5 to cause the LED group 14dG to emit lights. The light LT emitted upward from each LED 14d of the LED group 14dG passes through the relay lens 18 and reaches to the ring lens 8.

A space Vb to be a path of the light LT from the LED 14d to the ring lens 8 has a diameter direction outer side that is closed by the inner surface 2b1 of the stage portion 2b of the lid body 2, and a diameter direction inner side that is closed by the outer circumferential surface 10c1 of the stage base mount 16 and the stage base 10.

Namely, the space Vb is made to be a space in which the diameter direction side is closed and only the axial direction side open. A tip end portion on the axial direction side is closed by the ring lens 8.

By means of this, the emitted lights from the LED group 14dG will not reach to the fruit or vegetable AS without passing through the ring lens 8.

In FIG. 17, the main optical axis LTa of the light LT emitted from the LED 14d is indicated by a solid line.

When the main optical axis LTa passes through a center of the relay lens 18 and reaches to the light incoming surface 8b1 of the ring lens 8, because the light incoming surface 8b1 is inclined forward as it goes to the diameter direction outer side as shown in FIG. 8, the main optical axis LTa is emitted forward from the light outgoing surface 8b2 at an angle θb of the emitted light according that inclination angle θa and the refractive index of the material of the ring lens 8.

It is preferable to set the angle θb of the emitted light to be 0<θb<45°. Also, it is preferable to set the angle θb larger as much as the diameter Dc of the virtual reference circle P1 of the ring lens 8 is larger.

By means of this, it becomes easier for the lights LTR (to be described below) entered into the fruit or vegetable AS to be concentrated at a center in the interior of the fruit or vegetable AS.

In the case where the diameter Dc is approximately 40 mm as in the saccharinity meter 51, it is suitable for the angle θb to be about 20°.

The lights emitted forward from this light outgoing surface 8b2 becomes ring shaped lights LTR having a width in the in and out direction of the diameter and containing the main optical axis LTa.

Namely, in FIG. 17, among the ring shaped lights emitted from the light outgoing surface 8b2, a light path LTb from the LED 14d of the light emitted to be most deflected to the inner diameter side from the ring lens 8 is indicated by a dashed line. Also, a light path LTc from the LED 14d of the light emitted to be most deflected to the outer diameter side is indicated by a one dot chain line.

Moreover, in FIG. 17, the intensity characteristics Q of the ring shaped lights LTR at the front and rear direction position P2 after the emission are shown.

From these, the intensity characteristic Q in the diameter direction of the ring shaped lights LTR emitted from the ring lens 8 is a characteristic having a peak Qp that abruptly rises at the main optical axis LTa, in which the intensity is rapidly lowered as it goes toward the inner diameter side and the outer diameter side.

On the other hand, the intensity characteristic in the circumferential direction of the ring shaped lights LTR is almost constant.

Namely, the intensity characteristic in the circumferential direction of the ring shaped lights LTR is such that, even though the plurality of LEDs 14d are arranged to be separated in the circumferential direction, it is averaged to be almost the same level in the case where the plurality of LEDs 14d are turned on simultaneously, due to the emission characteristic of each LED 14d that is spread to the circumferential direction as well and the slight internal diffusion occurring in the relay lens 18 and the ring lens 8.

The ring shaped lights LTR emitted from the ring lens 8 have the main optical axis LTa that is deflected at the angle θb in the direction of approaching to the light receiving axial line CLT as described above (the light receiving axial line CLT is coinciding with the axial line of the light guide member 11).

In other words, the ring shaped lights LTR emitted from the ring lens 8 will be propagated to have the reduced diameter after emitted from the ring lens 8.

At the central portion on the inner side of the inner abutting portion 9, the front end surface 11a1 of the light guide member 11 is exposed.

(4) The lights LTR emitted from the ring lens 8 are irradiated in a ring shape onto the surface of the fruit or vegetable AS, and entering into the interior of the fruit or vegetable AS.

(5) The lights LTR entered into the interior of the fruit or vegetable AS are irregularly reflected in the interior while absorbed by the characteristic corresponding to a state of the fruit or vegetable AS, and a part of them is emitted to the external.

(6) The part of the lights emitted to the external enters into the interior of the light guide member 11 from the front end surface 11a1 of the light guide member 11 that is exposed to the external.

The lights entered into the interior of the light guide member 11 are those lights that are emitted from the LED group 14dG, passed through the interior of the fruit or vegetable AS, and returned, so that they are referred to as return lights LTd in the following.

The return lights LTd are propagated through the interior of the light guide member 11, and guided to the light guide protrusion portions 11f1011f7 of the leg portion 11f.

In this way, the return lights LTd are those lights that are propagated in a ring shape through the interior of the fruit or vegetable AS, reflected in the interior, and emitted to the external from the central portion with respect to the ring shaped entering portion at which they are entered. For this reason, even if there is a bias in the absorbance at each portion in the internal texture of the fruit or vegetable AS, they are going to be lights in which the bias is averaged.

Also, the lights LTR injected into the fruit or vegetable AS are in the ring shape, and deflected in the direction of approaching to the light receiving axial line CLT.

For this reason, among the lights irregularly reflected in the interior of the fruit or vegetable AS, a ratio of the lights injected into the front end surface 11a1 at the central lower portion becomes high compared with the case of not deflected (the angle θb=0).

By means of this, in the saccharinity meter 51, the return lights LTd are obtained at high efficiency with respect to the emitted lights of the LEDs 14d, so that even if there is a bias in the absorbance of the internal texture of the fruit or vegetable AS, they can be obtained as lights that are hard to be affected by that bias and reflecting the absorbance of the fruit or vegetable AS in higher precision.

(7) The return lights LTd guided to the light guide protrusion portions 11f1-11f7 of the leg portion 11f are uniform lights without the bias in the characteristics with each other, and they are emitted from the respective rear end surfaces 11fb of the respective engagement portions 11f1a-11f7a toward the band-pass filters 31-37, as the protrusion portion emitted lights LTe (LTe1-LTe7).

The rear end surface 11fb is going to be the rear end surface with respect to the front end surface 11a1 that is one end surface of its length in the light guide member 11.

(8) The protrusion portion emitted lights LTe emitted from the engagement portions 11f1a-11f7a are spectrally dispersed according to the respective spectral characteristics by the band-pass filters 31-37 and injected into the photo sensors 13c1-13c7.

(9) The photo sensors 13c1-13c7 detect the intensities Q1-Q7 that are the respective received light intensities, and send them out to the light intensity processing unit CT3 (see FIG. 14).

Namely, the intensities Q1-Q7 obtained from the photo sensors 13c1-13c7 are the spectral intensities of the central wavelengths λ1-λ7 of the band-pass filters 31-37 respectively.

(10) The light intensity processing unit CT3 obtains the absorbances of the wavelengths λ1-λ7 respectively by the known calculation method from the intensities Q1-Q7, and calculates the Brix value Y from each absorbance.

The exemplary concrete calculation method is as follows.

In general, the absorbance A of a wavelength λ is given by the equation (1), where IO (λ) is the intensity of light of a wavelength λ entering into the measurement target to be a reference, IS (λ) is the intensity of light of a wavelength λ emitted from the measurement target.

$$A = \log[IO(\lambda)/IS(\lambda)] \quad (1)$$
$$= \log IO(\lambda) - \log IS(\lambda)$$

Among seven types of wavelengths λ1-λ7, the wavelength λ6 is taken as a wavelength to be a reference, the absorbances A1-A5, A7 for the other six types of wavelengths λ1-λ5, λ7 respectively are obtained by the following equations (2-1)-(2-6).

$$A_1 = A(\lambda_1) - A(\lambda_6) = \log\frac{I_0(\lambda_1)}{I_s(\lambda_1)} - \log\frac{I_0(\lambda_6)}{I_s(\lambda_6)} \quad (2\text{-}1)$$

$$A_2 = A(\lambda_2) - A(\lambda_6) = \log\frac{I_0(\lambda_2)}{I_s(\lambda_2)} - \log\frac{I_0(\lambda_6)}{I_s(\lambda_6)} \quad (2\text{-}2)$$

...

$$A_6 = A(\lambda_7) - A(\lambda_6) = \log\frac{I_0(\lambda_7)}{I_s(\lambda_7)} - \log\frac{I_0(\lambda_6)}{I_s(\lambda_6)} \quad (2\text{-}6)$$

Based on these equations, the Brix value Y is calculated by the following equation (3).

$$Y = PL0 + A_1 \times PL1 + A_2 \times PL2 + A_3 \times PL3 + A_4 \times PL4 + A_5 \times PL5 + A_6 \times PL6 + T_1 \times PL7 + T_2 \times PL8$$

Here, PL0-PL8 are coefficiencts obtained in advance by the multiple regression analysis using the absorbance data for a plurality of measurement targets (fruit or vegetable AS). Also, the temperature T1 is a surface temperature of the measurement target (fruit or vegetable AS) measured by the temperature sensor 12, and the temperature T2 is a temperature corresponding to the casing K measured by the temperature sensor 12.

As shown in FIG. 14, the control unit CT has a correction unit CT2.

The correction unit CT2 makes the closed control of the light amount of the LED group 14dG, based on the light amount information JL from the FB photo sensor group 14eG and the temperature information JT from the temperature sensor 12.

As the general characteristic of the LED, the emitted light amount changes as the temperature increases. It is similar for the LEDs 14d.

The saccharinity meter 51 has the FB photo sensor group 14eG, the temperature sensor 12, and the correction unit CT2, so that the emitted light amount of the plurality of LEDs 14d can be made constant while it can be stabilized by suppressing variations in time. By means of this, the measurement precision of the saccharinity meter 51 is further improved.

The control unit CT is not limited to that which controls to cause all of the LEDs 14d of the LED group 14dG to emit lights simultaneously.

The control unit CT may cause the corresponding LEDs 14d to emit lights sequentially in time sequence, for each of six types of wavelengths that are set, or in an order of the arrangement in the circumferential direction, and measure the received light intensities of the photo sensors 13c1-13c7 in each occasion.

When the LED group 14dG is caused to emit lights simultaneously, the electricity consumption becomes large even in a short period of time, so that in the case where the reduction of the load on the power source is necessary, the latter method of causing the plurality of LEDs 14*d* to emit lights sequentially in time series and measuring is preferable.

The saccharinity meter 51 described above that is the nondestructive measurement apparatus for the fruit or vegetable uses the plurality of LEDs 14*d* as the light source of lights to be irradiated onto the fruit or vegetable AS.

By means of this, the saccharinity meter 51 requires less electricity consumption for the light source and less installment space, and can be made so compact that the casing K can be held by one hand.

Therefore, the measurement can be made easily even for the fruit or vegetable before the harvest that is still growing.

The saccharinity meter 51 has the plurality of LEDs 14*d* arranged in the circumferential direction, and the emitted light from each LED 14*d* is made to be irradiated toward the fruit or vegetable AS through the ring shaped ring lens 8. For this reason, the lights are made to be irradiated and injected as a ring shaped light bundle with respect to the fruit or vegetable AS.

By means of this, even if there is a bias in the absorbance of the internal texture of the fruit or vegetable AS, the averaged emitted lights that are hard to be affected by that bias can be obtained, and the measurement result that is well reflecting a state of the fruit or vegetable AS can be obtained.

The ring lens 8 is given with the optical characteristic in which the injected light from the LED 14*d* is deflected toward a center of the ring lens 8 and emitted.

For this reason, the intensities of the return lights that are reflected in the interior of the fruit or vegetable AS and emitted toward a central portion of the ring lens 8 can be obtained to be high, so that the utilization efficiency of the emitted lights of the LEDs 14*d* is high.

By means of this, the saccharinity meter 51 is suitable for a handy type which is capable of being made to have a low electricity consumption, and which is driven by a battery, by suppressing the emission light intensity for the fruit or vegetable with a high optical transparency and the like. Also, the return lights sufficient for the measurement can be easily obtained even for the fruit or vegetable with a low optical transparency due to a thick skin and the like, so that the saccharinity meter 51 has many types of the fruits and vegetables that can be measured and it is superior in versatility.

The saccharinity meter 51 has the ring shaped relay lens 18 for concentrating the lights from the LEDs 14*d* to the ring lens 8, in a middle of the emitted light path from the LEDs 14*d* to the ring lens 8.

As the relay lens 18 is arranged, the emitted lights of the LEDs 14*d* can be introduced to the ring lens 8 and irradiated onto the fruit or vegetable AS at higher efficiency.

Also by means of this, the saccharinity meter 51 becomes capable of being made to have a low electricity consumption, so that it is suitable for the handy type. Also, the return lights sufficient for the measurement can be obtained more easily even for the fruit or vegetable with a low optical transparency due to a thick skin and the like, so that the saccharinity meter 51 has many types of the fruits and vegetables that can be measured and it is superior in versatility.

Also, as the relay lens 18 is arranged, the light path distance between the LEDs 14*d* and the ring lens 8 can be made longer.

For this reason, the ring lens 8 can be arranged at a position closer with respect to the fruit or vegetable AS.

By means of this, the emitted light bundle from the ring lens 8 can be irradiated and injected onto the fruit or vegetable AS in a sufficiently narrow ring shape, so that the injected light intensity per unit area can be made higher. Consequently, the utilization efficiency of the emitted lights from the LEDs 14*d* is further improved.

Also, the influence due to the injected light from the external can be suppressed to a substantially ignorable level.

By means of this, the saccharinity meter 51 can carry out the measurement in high precision.

Also, as the light path distance between the LEDs 14*d* and the ring lens 8 can be made longer by arranging the relay lens 18, the stage portion on which the fruit or vegetable AS is to be mounted can be made to protrude sufficiently, with respect to the grip portion to be held by hand.

By means of this, as shown in FIG. 16, even in the case where the fruit or vegetable AS is measured by holding the grip portion K2, the fruit or vegetable AS and the fingers holding the grip portion K2 will not be abutted to each other, so that the operation can be carried out in good feel, easily, at high efficiency.

Also, when a slight displacement occurs in the implementation positions of the LEDs 14*d* on the base substrate 14 due to the unevenness in the manufacturing, a slight difference also occurs in the emitted light angle of each LED 14*d*. Also, in the case of using the packaged compound LEDs such as the 3-wavelength compound LEDs described above, the emitted light position is slightly different in the diameter direction for each emitted light central wavelength.

In contrast, the saccharinity meter 51 arranges the relay lens 18 as a reduction optical system lens between the LEDs 14*d* and the ring lens 8.

Namely, the relay lens 18 produces a reduction system of the light source from the lights emitted from the ring shaped light source (the plurality of LEDs 14*d* arranged in a ring shape), and inject it into the ring lens 8. Then the ring lens 8 is made to irradiate the injected reduction system of the light source onto the fruit or vegetable as ring shaped beams.

For this reason, even if the displacement occurs in the emitted light angle, in conjunction with the slight displacement in the implementation positions of the LEDs 14*d*, or the slight displacement in the diameter direction of the emitted light positions in the case where the LEDs 14*d* are the compound LEDs, an influence affecting the measurement by that displacement is small.

By means of this, the saccharinity meter 51 can carry out the measurement in high precision.

The saccharinity meter 51 has the inner abutting portion 9 and the outer abutting portion 7 respectively in the inner and outer positions in the diameter direction with respect to the ring lens 8.

By means of this, as shown in FIG. 17, a closed space Vc is formed by the ring lens 8, the fruit or vegetable AS, the inner abutting portion 9 and the outer abutting portion 7, in a state in which the fruit or vegetable AS is provided at the measurement portion K1.

Namely, on the outer diameter side with respect to the ring lens 8, a space between the stage portion 2*b* and the fruit or vegetable AS is closed by the outer abutting portion 7. Also, on the inner diameter side, a space between the stage portion 2*b* and the fruit or vegetable AS is closed by the inner abutting portion 9.

By means of this, the ring shaped lights LTR emitted from the ring lens 8 will not reach the front end surface 11*a*1 of the light guide member 11, and also will not be leaked to the external of the diameter outer side.

Consequently, the return lights LTd offered to the measurement in the saccharinity meter 51 are going to be lights incoming from the fruit or vegetable AS by necessity, so that the measurement precision is improved.

Also, as the lights LTR are not leaked to the external, the utilization efficiency of the emitted lights of the LEDs 14*d* is improved.

The saccharinity meter 51 is equipped with the light guide member 11 with its length in the light receiving axial line CLT direction, and one end side of the length of the light guide member 11 is made to be the front end surface 11*a*1 of the light incoming surface for the return lights LTd, and another end side is made to be the light outgoing surface for the return lights LTd toward the photo sensors 13*c*.

By means of this, the return lights LTd entered from the light incoming surface are guided to the light outgoing surface for a relatively long distance in conjunction with the inner surface reflection of the light guide member 11, so that the lights reached to the light outgoing surface become uniform lights regardless of positions reached on the light outgoing surfaces.

Consequently, the saccharinity meter 51 has no bias in the characteristics of lights incoming to the photo sensors 13*c*1-13*c*7 respectively, so that the measurement can be carried out at high precision.

With this configuration, the photo sensors 13*c*1-13*c*7 are arranged on a rear side, i.e., at farther positions from the outer abutting portion 7 and the inner abutting portion 9, than the LED group 14*d*G to be the light source, in the positional relationship in the front and rear direction within the casing K.

Consequently, the sensor substrate 13 on which the photo sensors 13*c*1-13*c*7 are mounted is arranged in vicinity of the rear surface 1*a* of the box body 1, and the light guide member 11 is arranged to be piercing through the hole 14*g* of the base substrate 14.

Next, the calibration of the saccharinity meter 51 will be described.

It is desired for the saccharinity meter 51 to carry out the calibration regularly, in order to maintain the measurement precision of the saccharinity meter 51 and more securely obtain a consistency with the measurement results of the other machines and of the past.

In the saccharinity meter 51, a standard lid body 52 for the purpose of that calibration is prepared.

Figure 18:
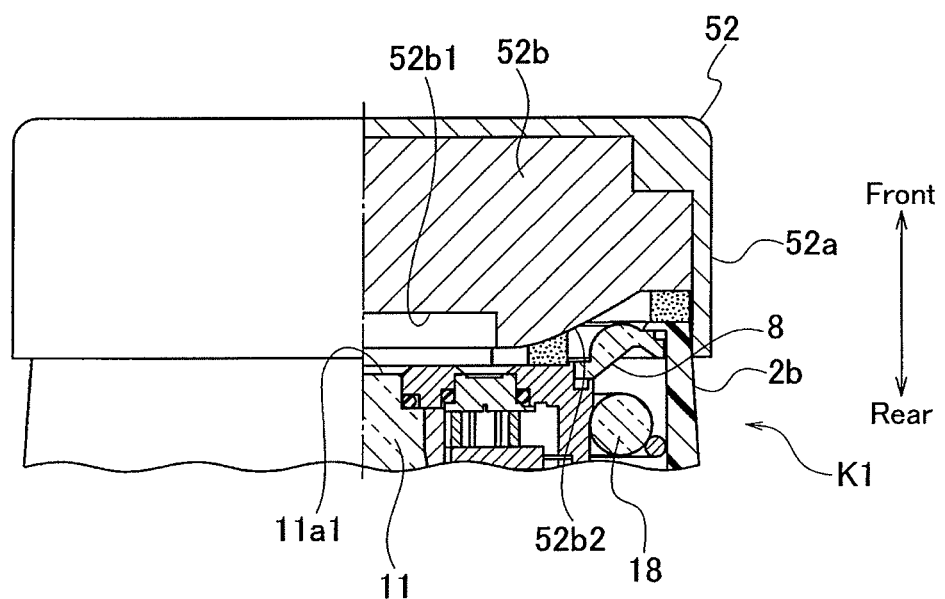
FIG. 18 is a half cross sectional view for explaining a standard lid body 52 to be used for a calibration of the saccharinity meter 51 of FIG. 1 and its state of use.

FIG. 18 is a half cross sectional view for explaining a state of use of the standard lid body 52, where the standard lid body 52 and a part of the measurement portion K1 in the casing K are shown.

The standard lid body 52 has a column shape covering a tip end opening of the measurement portion K1, and it is used by putting on the stage portion 2*b* of the lid body 2.

The standard lid body 52 has a round pot shaped base body 52*a*, and a reflection body 52*b* attached to an interior of the base body.

In the state of use shown in FIG. 18 the reflection body 52*b* is equipped with a concave portion 52*b*1 that is circularly depressed toward a front at a central portion, and a curved surface portion 52*b*2 having a ring shaped curved surface which is inclined such that it goes toward a front as it goes to the diameter direction outer side and a rear side becomes convex.

The concave portion 52*b*1 is opposing the front end surface 11*a*1 of the light guide member 11 in the front and rear direction, and the curved surface portion 52*b*2 is opposing the ring lens 8 at least in the light emission direction (a direction of the main optical axis LTa shown in FIG. 17).

The reflection body 52*b* is formed to be solid by a white material. The white material is a fluorocarbon resin, for example.

The reflection body 52*b* functions as a standard replacement for the fruit or vegetable to be measured.

Namely, the ring shaped lights LTR (see FIG. 17) emitted from the ring lens 8 are irradiated onto the curved surface portion 52*b*2 of the reflection body 52*b* and a part of them is entered into the interior.

The lights entered into the interior of the reflection body 52*b* are diffused in the interior and a part of them is emitted from the concave portion 52*b*1 to the external, and entered into the light guide member 11 as the return lights LTd.

The calibration is carried out by the light intensity processing unit CT3 and the central processing unit CT1, such that the measurement result based on these return lights LTd becomes the standard measurement value using the standard lid body 52, that is set in advance and stored in the memory unit CT6.

The measurement with the standard lid body 52 can be carried out by simply putting on the stage portion 2*b*, as the standard lid body 52 is small and easy to carry around. For this reason, the calibration operation is easy, and a correlation between one individual body and another individual body in the saccharinity meter 51 can be secured easily.

The embodiments of the present invention are not limited to the configuration and the procedure described above, and may be modified in a range not digressing from an essence of the present invention.

An embodiment of the saccharinity meter 51 may modify the configuration such that the return lights are positively diffused by providing a diffusion portion WB for diffusing the passing lights, on a path of the return lights in which the return lights passed through the fruit or vegetable AS and emitted are passed through the light guide member 11 and emitted from its rear end surface 11*f*b.

Namely, the diffusion portion WB may be provided between a portion enclosed by the ring shaped inner abutting portion 9 on a surface of the fruit or vegetable AS abutted to the inner abutting portion 9 and the rear end surface 11*f*b of the light guide member 11. Regarding this point, the modified examples 1-3 will be described next.

MODIFIED EXAMPLE 1

Figure 19:
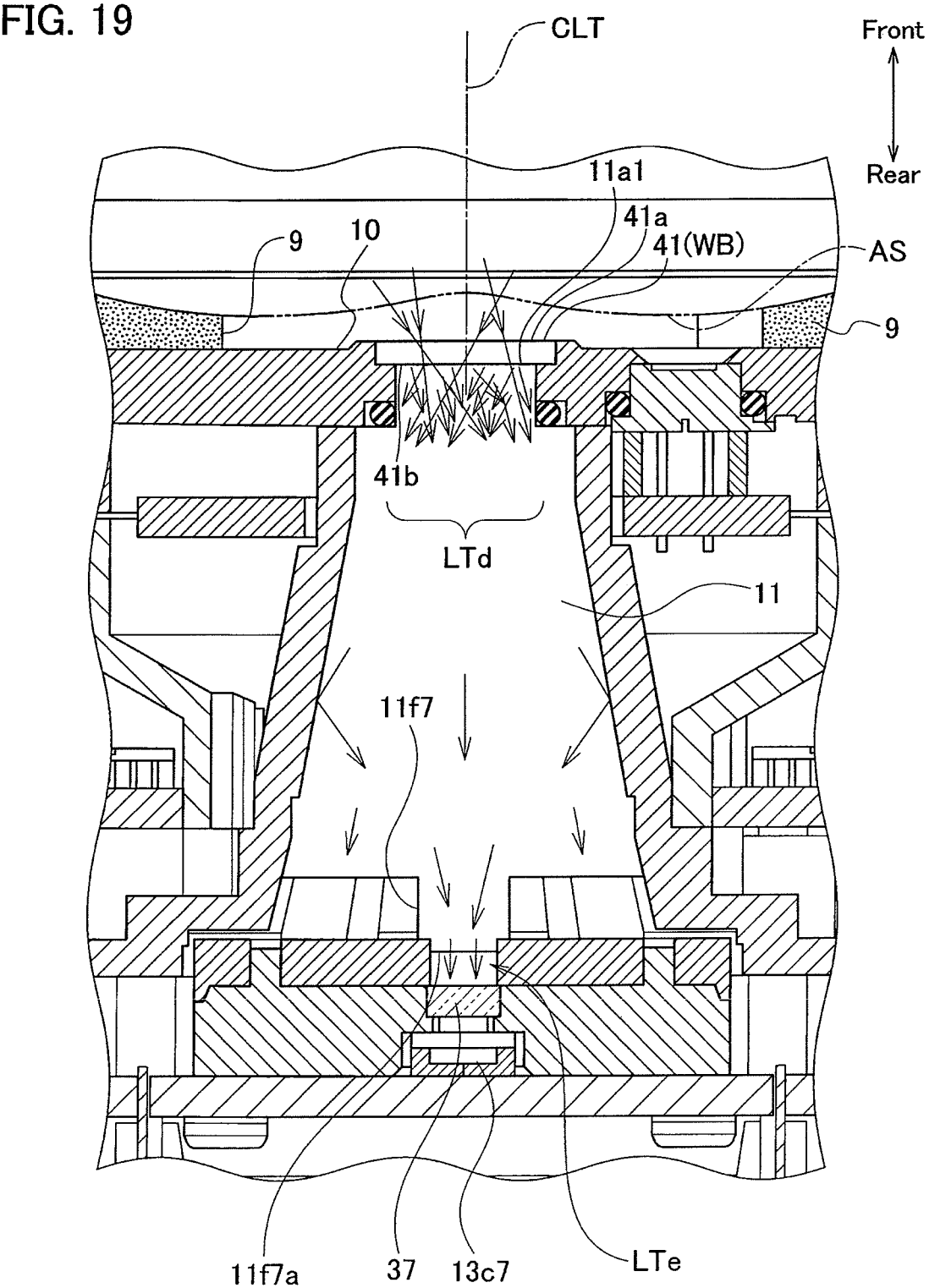
FIG. 19 is a partial cross sectional view for explaining a diffusion plate 41 as a modified example 1 of the saccharinity meter 51 of FIG. 1 and its attaching manner.

FIG. 19 is a partial cross sectional view for explaining a modified example 1, which is a diagram corresponding to the light guide member 11 and its vicinity in FIG. 17.

The modified example 1 is one in which a diffusion plate 41 is arranged in front of the front end surface 11*a*1 of the light guide member 11, in the saccharinity meter 51 of the embodiment.

More specifically, the diffusion plate 41 is attached to the stage base 10 by adhesive or double sided tape or the like, so as to cover an entire surface of the front end surface 11*a*1 in the front view.

The diffusion plate 41 diffuses the lights injected into a front surface 41*a* and emits them from a rear surface 41*b*.

A type of the diffusion plate 41 is not limited. For example, it is possible to apply the known diffusion plate, such as a diffusion plate formed in a plate shape by dispersing and compounding a diffusing agent in a transparent resin, or a diffusion plate in which a microlens is formed on at least one surface of a transparent resin plate, and the like.

In the modified example 1, as shown in FIG. 19, the return lights LTd are diffused and injected into the light guide member 11 from the front end surface 11a1, by the diffusion plate 41 arranged in front of the front end surface 11a1 of the light guide member 11.

By means of this, the return lights LTd that have passed through the fruit or vegetable AS and injected into the light guide member 11 are positively diffused to be more highly uniformized by the diffusion plate 41, and injected into the light guide member 11. After that, the uniformized return lights LTd are passing through the light guide member 11 and injected into the photo sensors 13c1-13c7 through the band-pass filters 31-37.

For this reason, the correlation coefficient between the absorbance and the Brix value Y is increased, and the measurement precision is improved such that the variations in the absorbance and the Brix value Y at a time of repeatedly measuring the identical fruit or vegetable AS are reduced, for example.

MODIFIED EXAMPLE 2

Figure 20:
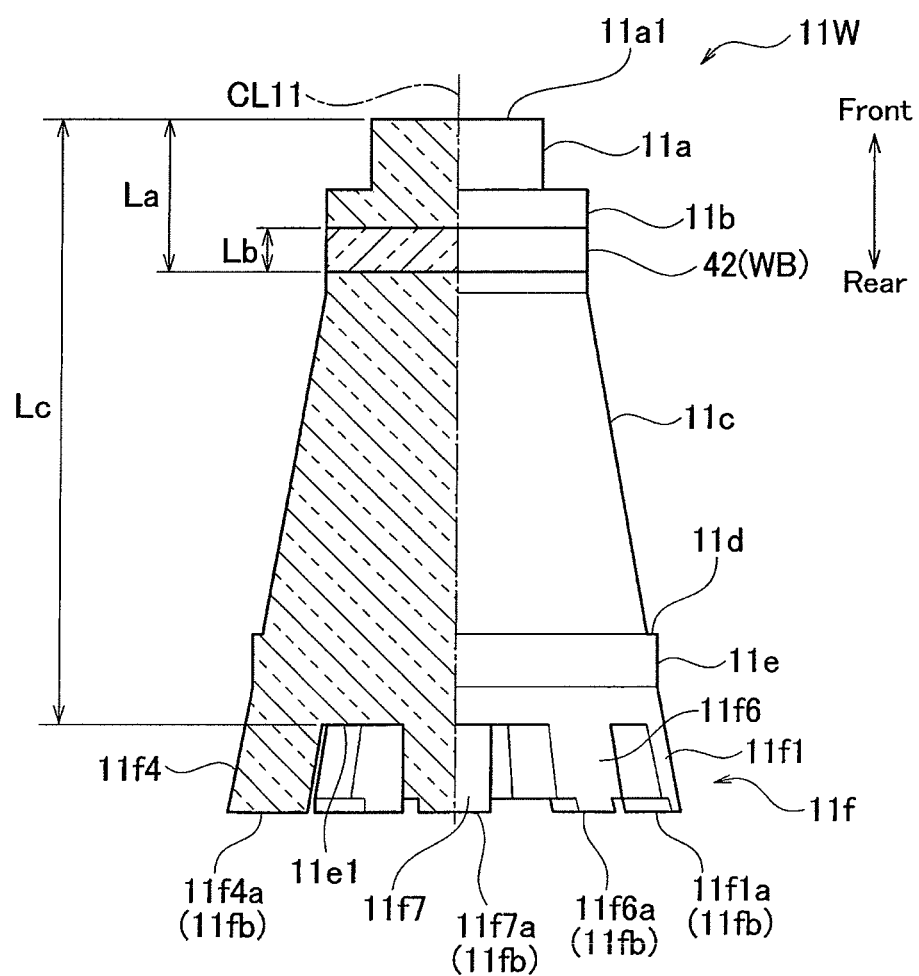
FIG. 20 is a half cross sectional view for explaining a light guide member 11W as a modified example 2 of the saccharinity meter 51 of FIG. 1.

The modified example 2 is one in which the light guide member 11W is applied, instead of the light guide member 11 used in the saccharinity meter 51. FIG. 20 is a half cross sectional view of the light guide member 11W.

In detail, the light guide member 11W is one in which a part in a direction of the axial line CL11 in the light guide member 11 is made to be a diffusion member 42.

Here, an example in which the light guide member 11W has a diffusion portion WB between the front end surface 11a1 and the rear surface 11e1 of the rear cylinder portion 11e (see FIG. 12) will be described.

In detail, the light guide member 11W has a diffusion member 42 of a thickness Lb, as the diffusion portion WB, with a position separated by a distance La from the front end surface 11a1 to a rear side as the rear end.

The diffusion member 42 is formed by dispersing and compounding a diffusing agent in a transparent resin, for example.

In the modified example 2, the return lights LTd (not shown in FIG. 20) injected from the front end surface 11a1 with respect to the light guide member 11W are injected from a front end of the diffusion member 42 and diffused and emitted to a rear side.

The maximum value of the distance La can take a distance Lc from the front end surface 11a1 to the rear surface 11e1 of the rear cylinder portion 11e. Namely, the distance La can be set in a range from the thickness Lb to the distance Lc. Also, the thickness of the diffusion member 42 can be set up to the distance La at maximum.

By means of this, the return lights LTd that passed through the fruit or vegetable AS and injected into the light guide member 11W are positively diffused to be more highly uniformized at a time of passing through the diffusion member 42 provided within the light guide member 11W. After that, the uniformized return lights LTd are emitted from the light guide member 11W, and injected into the photo sensors 13c1-13c7 through the band-pass filters 31-37.

For this reason, the correlation coefficient between the absorbance and the Brix value Y is increased, and the measurement precision is improved such that the variations in the absorbance and the Brix value Y at a time of repeatedly measuring the identical fruit or vegetable AS are reduced, for example.

Moreover, as the modified example 3, the light guide member 11WA formed by resin in which a diffusing agent is dispersed in the same shape may be applied, instead of the light guide member 11 used in the saccharinity meter 51 of the embodiment (see FIG. 12 for reference sign).

In this case, the return lights LTd injected into the light guide member 11WA are positively diffused to be more highly uniformized as they are propagated within the light guide member 11WA. After that, the uniformized return lights LTd are emitted from the light guide member 11WA, and injected into the photo sensors 13c1-13c7 through the band-pass filters 31-37. For this reason, the correlation coefficient between the absorbance and the Brix value Y is increased, and the measurement precision is improved such that the variations in the absorbance and the Brix value Y at a time of repeatedly measuring the identical fruit or vegetable AS are reduced, for example.

The modified examples 1-3 can be combined freely within a range in which combinations are possible.

In the embodiment and the modified examples 1-3, the relay lens 18 and the ring lens 8 may be an integrated single optical member.

The relay lens 18 and the ring lens 8 may be a plurality of optical members.

Namely, they may be an optical system configured by a single optical member or a plurality of optical members, for emitting the lights from the LEDs 14d, in a ring shape from a tip end of the measurement portion K1, and deflecting the emission direction, in a direction of approaching to the light receiving axial line CLT by an angle θb.

In the embodiment, one in which six types of LEDs 14d with six types among seven types of central wavelengths λ1-λ7 set to be their emission central wavelengths are used as the light source group 14dG has been described.

Of course, without being limited to this, the LED 14d may be used commonly with respect to the plurality of central wavelengths, in the case where it is judged that lights of the plurality of central wavelengths selected and set for the band-pass filters can be obtained at the optical intensities necessary for the measurement, based on the emission spectrum of the LED 14d that has one emission central wavelength or a broad emission spectrum.

Namely, with respect to the m (an integer greater than or equal to 2) types of wavelengths (λ1-λm) selected and set as the central wavelengths of the band-pass filters, q types of LEDs having q (1≤q≤m) types of emission central wavelengths respectively may be used.

In this case, it is equipped with at least m sets of the photo sensor 13c.

The light source is not limited to the LEDs, and may be other light emission elements.

The invention claimed is:
1. A nondestructive measurement apparatus, comprising:
a casing including a grip portion that is holdable in hand and a measurement portion having an outer ring shaped abutting portion that is configured to be abutted to a measurement target;
a light source group including a plurality of light sources arranged to be separated in a circumferential direction and in a ring shape in an interior of the casing;
a ring lens arranged in a ring shape smaller than an inner portion of the outer abutting portion surrounded by the outer abutting portion, the ring lens being configured to emit light coming from the light source group toward an outside of the casing as ring shaped light as a ring shaped beam;
a ring shaped relay lens that is configured to guide light from the light source group to the ring lens, between the light source group and the ring lens;

a light guide member having one end surface exposed to an inner side of the ring lens and another end surface positioned in the interior of the casing, the light guide member being configured to emit light, which is from the ring shaped light and has passed through the measurement target, incident from the one end surface to the another end surface;

photo sensors arranged inside the casing, the photo sensors being configured to detect light emitted from the another end surface of the light guide member; and a light intensity processor configured to obtain an absorbance according to detected intensities of the photo sensors, wherein the nondestructive measurement apparatus further comprises an inner ring-shaped abutting portion in an inner position in a diameter direction with respect to the ring lens, and wherein the inner abutting portion and the outer abutting portion are to be abutted to the measurement target such that a closed space is formed by the ring lens, the measurement target, the inner abutting portion, and the outer abutting portion.

2. The nondestructive measurement apparatus as described in claim 1, wherein the photo sensors include at least m sets of photo sensors (where m is an integer greater than or equal to 2), and the nondestructive measurement apparatus further comprises band-pass filters, each having a respective one of m types of different wavelengths $\lambda 1$-$\lambda m$ as a central wavelength, between a respective one of the m sets of photo sensors and the another end surface of the light guide member.

3. The nondestructive measurement apparatus as described in claim 2, wherein the light intensity processor is configured to obtain the absorbance according to the detected intensities respectively corresponding to the wavelengths $\lambda 1$-$\lambda m$ obtained by the m sets of the photo sensors, and to calculate a Brix value from the obtained absorbance.

4. The nondestructive measurement apparatus as described in claim 1, wherein the grip portion is formed to be holdable in hand by having a handle, and the measurement portion is formed such that an extending direction of the outer abutting portion is a direction along the handle, at one end portion of the handle in the grip portion, and a tip end surface of the outer abutting portion is positioned to be protruded from a surface of the grip portion.

5. A nondestructive measurement apparatus, comprising:

a casing including a grip portion that is holdable in hand and a measurement portion having a ring shaped abutting portion that is configured to be abutted to a measurement target;

a light source group including a plurality of light sources arranged to be separated in a circumferential direction in an interior of the casing to form a ring shaped light source;

a ring lens arranged in a ring shape smaller than an inner portion of the abutting portion surrounded by the abutting portion, the ring lens being configured to emit light coming from the light source group toward an outside of the casing as ring shaped light as ring shaped beam;

a light guide member having one end surface exposed to an inner side of the ring lens and another end surface positioned in the interior of the casing, the light guide member being configured to emit light, which is from the ring shaped light and has passed through the measurement target, incident from the one end surface to the another end surface;

photo sensors arranged inside the casing, the photo sensors being configured to detect light emitted from another end surface of the light guide member;

a light intensity processor configured to obtain an absorbance according to detected intensities of the photo sensors, and a ring shaped relay lens provided in a middle of an emitted light path from the light source group to the ring lens for concentrating the lights from the light source group to the ring lens, wherein the ring shaped relay lens is arranged as a reduction optical system lens for producing a reduction system of the light source from the lights emitted from the ring shaped light source in order to inject it into the ring lens and the ring lens is made to irradiate the injected reduction system of the light source onto the measurement target as ring shaped beams.

* * * * *